(12) United States Patent
Higuchi et al.

(10) Patent No.: US 7,442,696 B2
(45) Date of Patent: Oct. 28, 2008

(54) MINERALOCORTICOID RECEPTOR MODULATOR COMPOUNDS, PROCESSES FOR THEIR PREPARATION, AND THEIR USES

(75) Inventors: Robert I. Higuchi, Solana Beach, CA (US); Lin Zhi, San Diego, CA (US); Mark E. Adams, San Diego, CA (US); Yan Liu, San Diego, CA (US); Donald S. Karanewsky, Escondido, CA (US)

(73) Assignee: Ligand Pharmaceuticals, Inc., San Diego, CA (US)

( * ) Notice: Subject to any disclaimer, the term of this patent is extended or adjusted under 35 U.S.C. 154(b) by 33 days.

(21) Appl. No.: 11/622,983

(22) Filed: Jan. 12, 2007

(65) Prior Publication Data

US 2007/0197520 A1    Aug. 23, 2007

Related U.S. Application Data

(63) Continuation of application No. PCT/US2005/024748, filed on Jul. 12, 2005.

(60) Provisional application No. 60/587,947, filed on Jul. 14, 2004.

(51) Int. Cl.
*C07D 265/12* (2006.01)
*A61K 31/535* (2006.01)

(52) U.S. Cl. ..................... 514/230.5; 544/92

(58) Field of Classification Search ............ 544/92; 514/230.5
See application file for complete search history.

(56) References Cited

U.S. PATENT DOCUMENTS

| 5,171,851 | A | 12/1992 | Kim et al. |
|---|---|---|---|
| 5,874,430 | A | 2/1999 | Christ et al. |
| 6,436,929 | B1 * | 8/2002 | Zhang et al. ............ 514/230.5 |
| 6,444,668 | B1 | 9/2002 | Grubb et al. |
| 6,498,154 | B1 * | 12/2002 | Grubb et al. ............ 514/230.5 |
| 6,509,334 | B1 * | 1/2003 | Zhang et al. ............ 514/230.5 |

FOREIGN PATENT DOCUMENTS

| EP | 510235 | 10/1992 |
|---|---|---|
| WO | WO 98/14436 | 4/1998 |
| WO | WO 00/66164 | 11/2000 |
| WO | WO2005009969 | 2/2005 |

OTHER PUBLICATIONS

Zhang et al. Bioorganic & Medicinal Chemistry Letters 13 (2003), 1313-1316.*
Zhang, et al., "Novel 6-Aryl-1,4-dihydrobenzo[d][1,3]oxazine-2-thiones as Potent, Selective and Orally Active Nonsteroidal Progesterone Receptor Agonists", *Bioorg. Med. Chem. Lett.*, 2003, 13, 1313-1316.
Feb. 9, 2006 Written Opinion PCT_US2005_024749.
Feb. 9, 2006 International Search Report PCT_US2005_024749.
Jul. 24, 2006 Written Opinion PCT_US2005_024748.
Jul. 24, 2006 International Search Report PCT_US2005_024748.

* cited by examiner

*Primary Examiner*—Kahsay T Habte
(74) *Attorney, Agent, or Firm*—Knobbe Martens Olson & Bear LLP

(57) ABSTRACT

This invention relates to compounds that bind to mineralocorticoid receptors and/or modulate activity of mineralocorticoid receptors, and to methods for making and using such compounds. Some embodiments relate to compounds of Formula I:

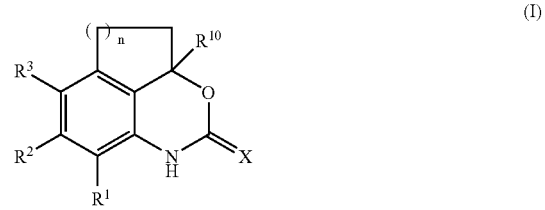

or a pharmaceutically acceptable salt, ester, amide, or prodrug thereof, wherein $R^1$—$R^{10}$ are as defined herein.

60 Claims, No Drawings

MINERALOCORTICOID RECEPTOR MODULATOR COMPOUNDS, PROCESSES FOR THEIR PREPARATION, AND THEIR USES

RELATED APPLICATIONS

This application is a continuation of co-pending Application No. PCT/US2005/024748, filed Jul. 12, 2005, which is a non-provisional of 60/587,947, filed Jul. 14, 2004, both of which are incorporated herein by reference in their entireties.

BACKGROUND OF THE INVENTION

1. Field of the Invention

This invention relates to compounds that bind to intracellular receptors and/or modulate activity of intracellular receptors, and to methods for making and using such compounds.

2. Description of the Related Art

Certain intracellular receptors (IRs) have been shown to regulate transcription of certain genes. See e.g. R. M. Evans, Science, 240, 889 (1988). Certain of such IRs are steroid receptors, such as androgen receptors, glucocorticoid receptors, estrogen receptors, mineralocorticoid receptors, and progesterone receptors. Gene regulation by such receptors typically involves binding of an IR by a ligand.

In certain instances, a ligand binds to an IR, forming a receptor/ligand complex. That receptor/ligand complex may then translocate to the nucleus of a cell, where it may bind to the DNA of one or more gene regulatory regions. Once bound to the DNA of a particular gene regulatory region, a receptor/ligand complex may modulate the production of the protein encoded by that particular gene. In certain instances, a mineralocorticoid receptor/ligand complex regulates expression of certain proteins. In certain instances, a mineralocorticoid receptor/ligand complex may interact directly with the DNA of a particular gene regulatory region. In certain instances, such interactions result in modulation of transcriptional activation.

SUMMARY OF THE INVENTION

In certain embodiments, the present invention provides a compound of Formula I:

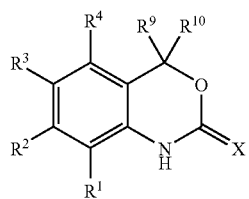

(I)

or a pharmaceutically acceptable salt, ester, amide, or prodrug thereof, wherein:

$R^1$ is selected from the group consisting of hydrogen, F, Cl, CN, $OR^{16}$, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^2$ is selected from the group consisting of hydrogen, F, Cl, CN, $OR^{16}$ an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^3$ is selected from the group consisting of (a), (b), (c), (d), (e), (f), (g), (h), (i), and (j):

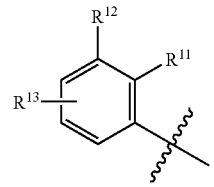

(a)

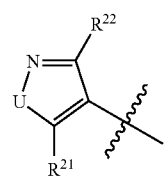

(b)

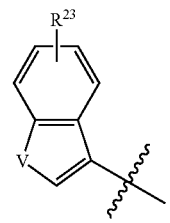

(c)

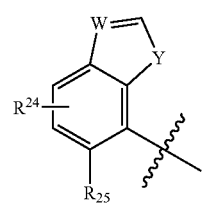

(d)

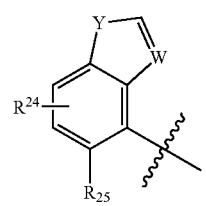

(e)

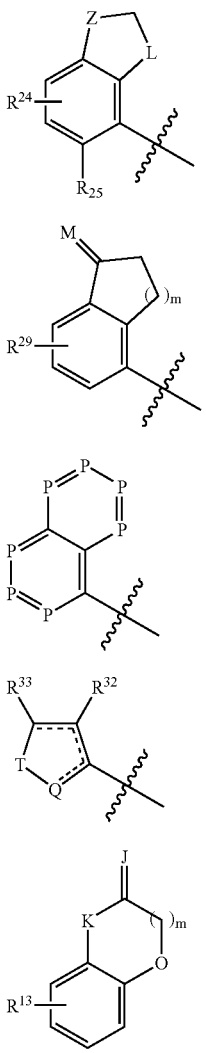

wherein,

R$^{11}$ is selected from the group consisting of F, Cl, CN, OR$^{16}$, NR$^{17}$R$^{18}$, CH$_2$R$^{16}$, COR$^{20}$, CO$_2$R$^{20}$, CONR$^{20}$R$^{20}$, SOR$^{20}$, or SO$_2$R$^{20}$, an optionally substituted C$_1$-C$_8$ alkyl, an optionally substituted C$_1$-C$_8$ heteroalkyl, an optionally substituted C$_1$-C$_8$ haloalkyl, an optionally substituted C$_1$-C$_8$ heterohaloalkyl, an optionally substituted C$_3$-C$_8$ cycloalkyl, an optionally substituted C$_2$-C$_8$ heterocycle, an optionally substituted C$_5$-C$_8$ aryl, and an optionally substituted C$_3$-C$_8$ heteroaryl;

R$^{12}$ is selected from the group consisting of hydrogen F, Cl, CN, COR$^{20}$, CO$_2$R$^{20}$, CONR$^{20}$R$^{20}$, NO$_2$, OR$^{16}$, NR$^{17}$R$^{18}$, SOR$^{20}$ or SO$_2$R$^{20}$, an optionally substituted C$_1$-C$_8$ alkyl, an optionally substituted C$_1$-C$_8$ heteroalkyl, an optionally substituted C$_1$-C$_8$ haloalkyl, an optionally substituted C$_1$-C$_8$ heterohaloalkyl, an optionally substituted C$_3$-C$_8$ cycloalkyl, an optionally substituted C$_2$-C$_8$ heterocycle, an optionally substituted C$_5$-C$_8$ aryl, and an optionally substituted C$_3$-C$_8$ heteroaryl;

R$^{13}$ is selected form hydrogen, F, Cl, CN, and OR$^{16}$, an optionally substituted C$_1$-C$_8$ alkyl, an optionally substituted C$_1$-C$_8$ heteroalkyl, an optionally substituted C$_1$-C$_8$ haloalkyl, an optionally substituted C$_1$-C$_8$ heterohaloalkyl, an optionally substituted C$_3$-C$_8$ cycloalkyl, an optionally substituted C$_2$-C$_8$ heterocycle, an optionally substituted C$_5$-C$_8$ aryl, and an optionally substituted C$_3$-C$_8$ heteroaryl;

R$^{21}$ is selected from the group consisting of hydrogen, an optionally substituted C$_1$-C$_8$ alkyl, an optionally substituted C$_1$-C$_8$ heteroalkyl, an optionally substituted C$_1$-C$_8$ haloalkyl, an optionally substituted C$_1$-C$_8$ heterohaloalkyl, an optionally substituted C$_3$-C$_8$ cycloalkyl, an optionally substituted C$_2$-C$_8$ heterocycle, an optionally substituted C$_5$-C$_8$ aryl, and an optionally substituted C$_3$-C$_8$ heteroaryl;

R$^{22}$ is selected from the group consisting of F, Cl, OR$^{16}$, NR$^{17}$R$^{18}$, an optionally substituted C$_1$-C$_8$ alkyl, an optionally substituted C$_1$-C$_8$ heteroalkyl, an optionally substituted C$_1$-C$_8$ haloalkyl, an optionally substituted C$_1$-C$_8$ heterohaloalkyl, an optionally substituted C$_3$-C$_8$ cycloalkyl, an optionally substituted C$_2$-C$_8$ heterocycle, an optionally substituted C$_5$-C$_8$ aryl, and an optionally substituted C$_3$-C$_8$ heteroaryl;

R$^{23}$ is selected from the group consisting of hydrogen, F, Cl, OR$^{16}$, an optionally substituted C$_1$-C$_8$ alkyl, an optionally substituted C$_1$-C$_8$ heteroalkyl, an optionally substituted C$_1$-C$_8$ haloalkyl, an optionally substituted C$_1$-C$_8$ heterohaloalkyl, an optionally substituted C$_3$-C$_8$ cycloalkyl, an optionally substituted C$_2$-C$_8$ heterocycle, an optionally substituted C$_5$-C$_8$ aryl, and an optionally substituted C$_3$-C$_8$ heteroaryl;

R$^{24}$ is selected from the group consisting of hydrogen, F, Cl, and OR$^{16}$;

R$^{25}$ is selected from the group consisting of hydrogen, F, Cl, OR$^{16}$, CN, an optionally substituted C$_1$-C$_8$ alkyl, an optionally substituted C$_1$-C$_8$ heteroalkyl, an optionally substituted C$_1$-C$_8$ haloalkyl, an optionally substituted C$_1$-C$_8$ heterohaloalkyl, an optionally substituted C$_3$-C$_8$ cycloalkyl, an optionally substituted C$_2$-C$_8$ heterocycle, an optionally substituted C$_5$-C$_8$ aryl, and an optionally substituted C$_3$-C$_8$ heteroaryl;

R$^{29}$ is selected from the group consisting of hydrogen, F, Cl, and OR$^{16}$;

R$^{32}$ and R$^{33}$ are each independently selected from the group consisting of hydrogen, F, Cl, OR$^{16}$, CN, COR$^{20}$, an optionally substituted C$_1$-C$_8$ alkyl an optionally substituted C$_1$-C$_8$ heteroalkyl, an optionally substituted C$_1$-C$_8$ haloalkyl, an optionally substituted C$_1$-C$_8$ heterohaloalkyl, an optionally substituted C$_3$-C$_8$ cycloalkyl, an optionally substituted C$_2$-C$_8$ heterocycle, an optionally substituted C$_5$-C$_8$ aryl, and an optionally substituted C$_3$-C$_8$ heteroaryl;

U is selected from the group consisting of O, and NR$^{17}$;
V is selected from the group consisting of O, S, and NR$^{17}$;
W is selected from the group consisting of CR$^{27}$ and N;
Y is selected from the group consisting of NR$^{26}$, S and O;
Z and L are each selected from the group consisting of CH$_2$, NR$^{28}$, and O wherein
  either Z is CH$_2$ and L is selected from the group consisting of NR$^{28}$ and O,
  or L is CH$_2$ and Z is selected from the group consisting of NR$^{28}$ and O;
M is selected from the group consisting of O and NOR$^{30}$;
each P is independently selected from the group consisting of N and CR$^{31}$, provided that no more than two of the Ps are N;
Q and T are each selected from the group consisting of S, NR$^{17}$, and CR$^{34}$ wherein
  either Q is CR$^{34}$ and T is selected from the group consisting of S, O, NR$^{17}$, or T is $CR^{34}$ and Q is selected from the group consisting of S, O, $NR^{17}$;

K is selected from the group consisting of O and $NR^{35}$;

J is selected from the group consisting of O and S; and m is selected from 1 and 2;

$R^4$ is selected from the group consisting of hydrogen, F, Cl, Br, I, $NO_2$, $OR^9$, $NR^{10}R^{11}$, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^9$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{10}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl; and X is selected from the group consisting of O, S, and $NOR^{16}$;

wherein, at least one of $R^1$, $R^2$ and $R^4$ is not hydrogen;

$R^{16}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{17}$ and $R^{18}$ are independently selected from the group consisting of hydrogen, $COR^{20}$, $CO_2R^{20}$, $SO_2R^{20}$, $S(O)R^{20}$, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{20}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{26}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{27}$ is selected from the group consisting of hydrogen, F, Cl, Br, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{28}$ is selected from the group consisting of hydrogen, $COR^{20}$, $CO_2R^{20}$, $CONR^{20}$, $SO_2R^{20}$, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{30}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{31}$ is selected from the group consisting of hydrogen, F, Cl, and $OR^{16}$;

$R^{34}$ is selected from the group consisting of hydrogen, F, Cl, $NO_2$, $OR^{16}$, $NR^{17}R^{18}$, CN, $COR^{20}$, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl; and $R^{35}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl.

In certain embodiments, the present invention provides a compound of Formula I:

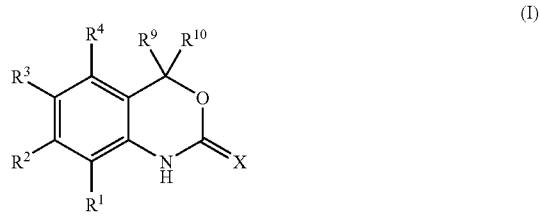

(I)

or a pharmaceutically acceptable salt, ester, amide, or prodrug thereof, wherein:

$R^1$ is selected from the group consisting of hydrogen, F, Cl, CN, $OR^{16}$, methyl, and trifluoromethyl;

$R^2$ is selected from the group consisting of hydrogen, F, Cl, CN, $OR^{16}$, methyl, or trifluoromethyl;

$R^3$ is selected from the group consisting of (a), (b), (c), (d), (e), (f), (g), (h), (i), and (j):

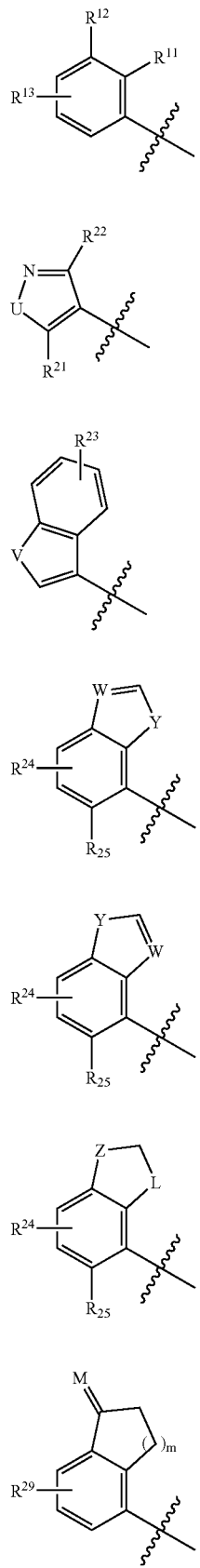

(a)

(b)

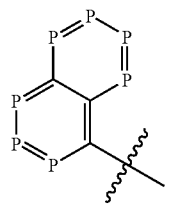

(h)

(i)

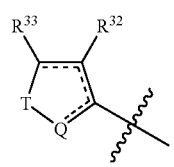

(j)

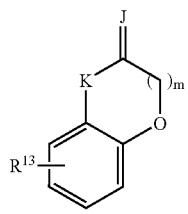

wherein,

R[11] is selected from the group consisting of F, Cl, CN, OR[16], NR[17]R[18], CH$_2$R[16], COR[20], CO$_2$R[20], CONR[20]R[20], SOR[20], or SO$_2$R[20], an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

R[12] is selected from the group consisting of hydrogen, methyl, trifluoromethyl, F, Cl, CN, COR[20], CO$_2$R[20], CONR[20]R[20], SOR[20], SO$_2$R[20], NO$_2$, OR[16], NR[17]R[18];

R[13] is selected form hydrogen, methyl, trifluoromethyl, F, Cl, CN, and OR[16];

R[21] is selected from the group consisting of hydrogen, methyl, and trifluoromethyl;

R[22] is selected from the group consisting of F, Cl, OR[16], NR[17]R[18], an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

R[23] is selected from the group consisting of hydrogen, F, Cl, methyl, trifluoromethyl, and OR[16];

R[24] is selected from the group consisting of hydrogen, F, Cl, and OR[16];

R[25] is selected from the group consisting of hydrogen, F, Cl, OR[16], CN, methyl and trifluoromethyl;

R[29] is selected from the group consisting of hydrogen, F, Cl, and OR[16];

$R^{32}$ and $R^{33}$ are each independently selected from the group consisting of hydrogen, F, Cl, $OR^{16}$, CN, $COR^{20}$, methyl and trifluoromethyl;

U is selected from the group consisting of O and $NR^{17}$;

V is selected from the group consisting of O, S, and $NR^{17}$;

W is selected from the group consisting of $CR^{27}$ and N;

Y is selected from the group consisting of $NR^{26}$, S and O;

Z and L are each selected from the group consisting of $CH_2$, $NR^{28}$, and O wherein
- either Z is $CH_2$ and L is selected from the group consisting of $NR^{28}$ and O,
- or L is $CH_2$ and Z is selected from the group consisting of $NR^{28}$ and O;

M is selected from the group consisting of O and $NOR^{30}$;

each P is independently selected from the group consisting of N and $CR^{31}$, provided that no more than two of the Ps are N;

Q and T are each selected from the group consisting of S, $NR^{17}$, and $CR^{34}$ wherein
- either Q is $CR^{34}$ and T is selected from the group consisting of S, O, $NR^{17}$,
- or T is $CR^{34}$ and Q is selected from the group consisting of S, O $NR^{17}$;

K is selected from the group consisting of O and $NR^{35}$;

J is selected from the group consisting of O and S; and m is selected from 1 and 2;

$R^4$ is selected from the group consisting of hydrogen, F, Cl, Br, I, $NO_2$, $OR^9$, $NR^{10}R^{11}$, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^9$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{10}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl; and X is selected from the group consisting of O, S, and $NOR^{16}$;

wherein,
at least one of $R^1$, $R^2$ or $R^4$ is not hydrogen;

$R^{16}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{17}$ and $R^{18}$ are independently selected from the group consisting of hydrogen, $COR^{20}$, $CO_2R^{20}$, $SO_2R^{20}$, $S(O)R^{20}$, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{20}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{26}$ is selected from the group consisting of hydrogen, methyl, and trifluoromethyl;

$R^{27}$ is selected from the group consisting of hydrogen, F, Cl, Br, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl;

$R^{28}$ is selected from the group consisting of hydrogen, methyl, $COR^{20}$, $CO_2R^{20}$, $CONR^{20}$, and $SO_2R^{20}$;

$R^{30}$ is selected from the group consisting of hydrogen and methyl;

$R^{31}$ is selected from the group consisting of hydrogen, F, Cl, and $OR^{16}$;

$R^{34}$ is selected from the group consisting of hydrogen, F, Cl, $NO_2$, $OR^{16}$, $NR^{17}R^{18}$, CN, $COR^{20}$, methyl, and trifluoromethyl; and $R^{35}$ is selected from the group consisting of hydrogen, an optionally substituted $C_1$-$C_8$ alkyl, an optionally substituted $C_1$-$C_8$ heteroalkyl, an optionally substituted $C_1$-$C_8$ haloalkyl, an optionally substituted $C_1$-$C_8$ heterohaloalkyl, an optionally substituted $C_3$-$C_8$ cycloalkyl, an optionally substituted $C_2$-$C_8$ heterocycle, an optionally substituted $C_5$-$C_8$ aryl, and an optionally substituted $C_3$-$C_8$ heteroaryl.

In certain embodiments, the invention provides a compound that is a 2H-3,1-benzoxazine-2-one. In certain embodiments, the invention provides a compound that is derived from a 2H-3,1-benzoxazine-2-one. In certain embodiments, the invention provides a compound that is a 2H-3,1-benzoxazine-2-thione. In certain embodiments, the invention provides a compound that is derived from a 2H-3,1-benzoxazine-2-thione. In certain embodiments, the invention provides a compound that is a 6-aryl-2H-3,1-benzoxazine-2-one. In certain embodiments, the invention provides a compound that is a 6-aryl-2H-3,1-benzoxazine-2-thione.

In certain embodiments, the invention provides a selective mineralocorticoid receptor modulator. In certain embodiments, the invention provides a selective mineralocorticoid receptor agonist. In certain embodiments, the invention provides a selective mineralocorticoid receptor antagonist. In certain embodiments, the invention provides a selective mineralocorticoid receptor partial agonist. In certain embodiments, the invention provides a selective mineralocorticoid receptor binding compound.

In certain embodiments, the invention provides a pharmaceutical agent comprising a physiologically acceptable carrier, diluent, and/or excipient; and one or more compounds of the present invention.

In certain embodiments, the invention provides a compound for treating a patient. In certain embodiments, the invention provides a compound for the treatment of a condition selected from the group consisting of, congestive heart failure, hypertension, fibrosis (including, but not limited to, cardiac, kidney, and lung), primary hyperaldosteronism, hypokalemia, and liver cirrhosis. In certain such embodiments, the patient suffers from a condition including, but not limited to, hypoaldosteronism, hyperkalemia, metabolic acidosis, hypoadrenocorticoidism, and Addision's disease.

In certain embodiments, the invention provides a method for modulating at least one activity of a mineralocorticoid receptor. Certain such methods comprise contacting a mineralocorticoid receptor with one or more compounds of the present invention.

In certain embodiments, the invention provides a method for identifying a compound that is capable of modulating activity of a mineralocorticoid receptor comprising contacting a cell expressing the mineralocorticoid receptor with a compound of the present invention and monitoring an effect on the cell.

In certain embodiments, the invention provides a method of treating a patient comprising administering to the patient a compound of the present invention. In certain embodiments, the invention provides a method of treating a condition including, but not limited to, congestive heart failure, hypertension, fibrosis (including, but not limited to, cardiac, kidney, and lung), primary hyperaldosteronism, hypokalemia, and liver cirrhosis. In certain embodiments, the invention provides a method of treating a condition including, but not limited to, hypoaldosteronism, hyperkalemia, metabolic acidosis, hypoadrenocorticoidism, and Addision's disease.

DETAILED DESCRIPTION

It is to be understood that both the foregoing general description and the following detailed description are exemplary and explanatory only and are not restrictive of the invention claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definitions

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g. electroporation, lipofection). Reactions and purification techniques may be performed e.g. using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g. Sambrook et al. Molecular Cloning: A Laboratory Manual (2d ed., Cold Spring Harbor Laboratory Press, Cold Spring Harbor, N.Y. (1989)), which is incorporated herein by reference for any purpose.

As used herein, the following terms are defined with the following meanings, unless expressly stated otherwise.

The term "selective binding compound" refers to a compound that selectively binds to any portion of one or more target receptors.

The term "selective mineralocorticoid receptor binding compound" refers to a compound that selectively binds to any portion of a mineralocorticoid receptor.

The term "selectively binds" refers to the ability of a selective binding compound to bind to a target receptor with greater affinity than it binds to a non-target receptor. In certain embodiments, selective binding refers to binding to a target with an affinity that is at least 10, 50, 100, 250, 500, or 1000 times greater than the affinity for a non-target.

The term "target receptor" refers to a receptor or a portion of a receptor capable of being bound by a selective binding compound. In certain embodiments, a target receptor is a mineralocorticoid receptor.

The term "modulator" refers to a compound that alters an activity of a molecule. For example, a modulator may cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "selective modulator" refers to a compound that selectively modulates a target activity.

The term "selective mineralocorticoid receptor modulator" refers to a compound that selectively modulates at least one activity associated with a mineralocorticoid receptor.

The term "selectively modulates" refers to the ability of a selective modulator to modulate a target activity to a greater extent than it modulates a non-target activity.

The term "target activity" refers to a biological activity capable of being modulated by a selective modulator. Certain exemplary target activities include, but are not limited to, binding affinity, signal transduction, enzymatic activity, tumor growth, and inflammation or inflammation-related processes.

The term "receptor mediated activity" refers any biological activity that results, either directly or indirectly, from binding of a ligand to a receptor.

The term "agonist" refers to a compound, the presence of which results in a biological activity of a receptor that is the same as the biological activity resulting from the presence of a naturally occurring ligand for the receptor.

The term "partial agonist" refers to a compound the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "alkyl" refers to an aliphatic hydrocarbon group. An alkyl may be a "saturated alkyl," which means that it does not contain any alkene or alkyne groups. An alkyl group may be an "unsaturated alkyl," which means that it comprises at least one alkene or alkyne group. An alkyl, whether saturated or unsaturated, may be branched or straight chain. Alkyls may be substituted or unsubstituted. Alkyls include, but are not limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like, each of which may be optionally substituted.

In certain embodiments, an alkyl comprises 1 to 20 carbon atoms (whenever it appears herein, a numerical range such as "1 to 20" refers to each integer in the given range; e.g. "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated).

The term "lower alkyl" refers to an alkyl comprising 1 to 5 carbon atoms. The term "medium alkyl" refers to an alkyl comprising 5 to 10 carbon atoms. An alkyl may be designated as "$C_1$-$C_4$ alkyl" or similar designations. By way of example only, "$C_1$-$C_4$ alkyl" indicates an alkyl having one, two, three, or four carbon atoms (e.g., methyl, ethyl, propyl, iso-propyl, n-butyl, iso-butyl, sec-butyl, t-butyl, ethenyl, propenyl, butenyl, ethynyl, propynyl, and butynyl).

The term "alkenyl" refers to an alkyl group comprising at least one carbon-carbon double bond.

The term "alkynyl" refers to an alkyl group comprising at least one carbon-carbon triple bond.

The term "haloalkyl" refers to an alkyl in which at least one hydrogen atom is replaced with a halogen atom. In certain of the embodiments in which two or more hydrogen atom are replaced with halogen atoms, the halogen atoms are all the same as one another. In certain of such embodiments, the halogen atoms are not all the same as one another.

The term "heteroalkyl" refers to a group comprising an alkyl and one or more heteroatoms. Certain heteroalkyls are acylalkyls, in which the one or more heteroatoms are within an alkyl chain. Certain other heteroalkyls are acylalkyls, in which the heteroatom is not within the alkyl chain. Examples of heteroalkyls include, but are not limited to, $CH_3C(=O)CH_2-$, $CH_3C(=O)CH_2CH_2-$, $CH_3CH_2C(=O)CH_2CH_2-$, $CH_3C(=O)CH_2CH_2CH_2-$, $CH_3OCH_2CH_2-$, $CH_3NHCH_2-$, and the like.

The term "heterohaloalkyl" refers to a heteroalkyl in which at least one hydrogen atom is replaced with a halogen atom.

The term "carbocycle" refers to a group comprising a covalently closed ring, wherein each of the atoms forming the ring is a carbon atom. Carbocyclic rings may be formed by three, four, five, six, seven, eight, nine, or more than nine carbon atoms. Carbocycles may be optionally substituted.

The term "heterocycle" refers to a group comprising a covalently closed ring wherein at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). In heterocyclic rings comprising two or more heteroatoms, those two or more heteroatoms may be the same or different from one another. Heterocycles may be optionally substituted. Binding to a heterocycle can be at a heteroatom or via a carbon atom. For example, binding for benzo-fused derivatives, may be via a carbon of the benzenoid ring. Examples of heterocycles include, but are not limited to the following:

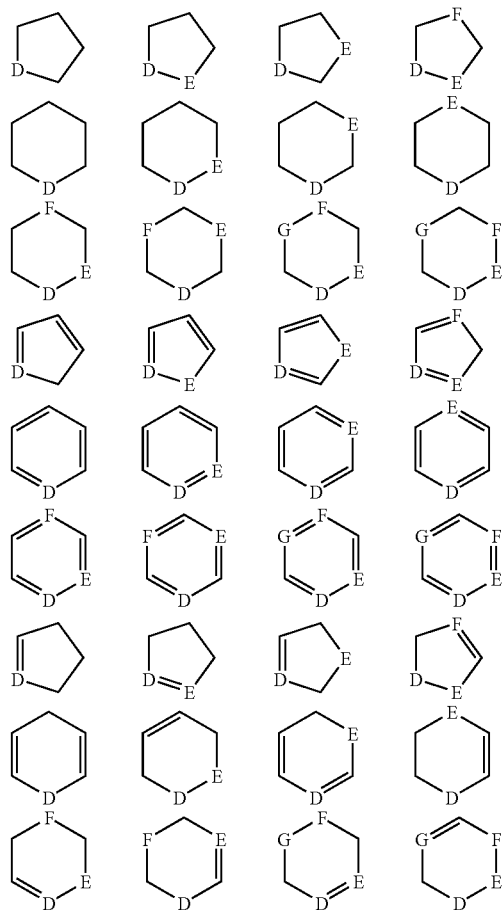

wherein D, E, F, and G independently represent a heteroatom. Each of D, E, F, and G may be the same or different from one another.

The term "heteroatom" refers to an atom other than carbon or hydrogen. Heteroatoms are typically independently selected from the group consisting of oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed ring having a delocalized π-electron system. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from the group consisting of an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, a sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic group wherein at least one atom forming the aromatic ring is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from the group consisting of halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "non-aromatic ring" refers to a group comprising a covalently closed ring that does not have a delocalized π-electron system.

The term "cycloalkyl" refers to a group comprising a non-aromatic ring wherein each of the atoms forming the ring is a carbon atom. Cycloalkyl rings may be formed by three, four, five, six, seven, eight, nine, or more than nine carbon atoms. Cycloalkyls may be optionally substituted. In certain embodiments, a cycloalkyl comprises one or more unsaturated bonds. Examples of cycloalkyls include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "arylalkyl" refers to a group comprising an aryl group bound to an alkyl group.

The term "carbocycloalkyl" refers to a group comprising a carbocyclic cycloalkyl ring. Carbocycloalkyl rings may be formed by three, four, five, six, seven, eight, nine, or more than nine carbon atoms. Carbocycloalkyl groups may be optionally substituted.

The term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g. cycloalkyls and non-aromatic heterocycles). Rings may be optionally substituted. Rings may form part of a ring system.

The term "ring system" refers to two or more rings, wherein two or more of the rings are fused. The term "fused" refers to structures in which two or more rings share one or more bonds.

The substituent "R" appearing by itself and without a number designation refers to a substituent selected from the group consisting of alkyl, cycloalkyl, aryl, heteroaryl (bonded through a ring carbon) and non-aromatic heterocycle (bonded through a ring carbon).

The term "O-carboxy" refers to a group of formula RC(=O)O—.

The term "C-carboxy" refers to a group of formula —C(=O)OR.

The term "acetyl" refers to a group of formula —C(=O)CH$_3$.

The term "trihalomethanesulfonyl" refers to a group of formula X$_3$CS(=O)$_2$— where X is a halogen.

The term "cyano" refers to a group of formula —CN.

The term "isocyanato" refers to a group of formula —NCO.

The term "thiocyanato" refers to a group of formula —CNS.

The term "isothiocyanato" refers to a group of formula —NCS.

The term "sulfonyl" refers to a group of formula —S(=O)—R.

The term "S-sulfonamido" refers to a group of formula —S(=O)$_2$NR.

The term "N-sulfonamido" refers to a group of formula RS(=O)$_2$NH—.

The term "trihalomethanesulfonamido" refers to a group of formula X$_3$CS(=O)$_2$NR—.

The term "O-carbamyl" refers to a group of formula —OC(=O)—NR.

The term "N-carbamyl" refers to a group of formula ROC(=O)NH—.

The term "O-thiocarbamyl" refers to a group of formula —OC(=S)—NR.

The term "N-thiocarbamyl" refers to a group of formula ROC(=S)NH—.

The term "C-amido" refers to a group of formula —C(=O)—NR$_2$.

The term "N-amido" refers to a group of formula RC(=O)NH—.

The term "ester" refers to a chemical moiety with formula —(R)$_n$—COOR', where R and R' are independently selected from the group consisting of alkyl, cycloalkyl, aryl, heteroaryl (bonded through a ring carbon) and non-aromatic heterocycle (bonded through a ring carbon), where n is 0 or 1.

The term "amide" refers to a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), where n is 0 or 1. In certain embodiments, an amide may be an amino acid or a peptide.

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

Unless otherwise indicated, the term "optionally substituted," refers to a group in which none, one, or more than one of the hydrogen atoms has been replaced with one or more group(s) individually and independently selected from the group consisting of: alkyl, heteroalkyl, haloalkyl, heterohaloalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and disubstituted amino groups, and the protected derivatives of amino groups. Such protective derivatives (and protecting groups that may form such protective derivatives) are known to those of skill in the art and may be found in references such as Greene and Wuts, above. In embodiments in which two or more hydrogen atoms have been substituted, the substituent groups may together form a ring.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "prodrug" refers to a pharmaceutical agent that is converted from a less active form into a corresponding more active form in vivo.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

The term "tissue-selective" refers to the ability of a compound to modulate a biological activity in one tissue to a greater or lesser degree than it modulates a biological activity in another tissue. The biological activities in the different tissues may be the same or they may be different. The biological activities in the different tissues may be mediated by the same type of target receptor. For example, in certain embodiments, a tissue-selective compound may modulate a mineralocorticoid receptor mediated biological activity in one tissue and fail to modulate, or modulate to a lesser degree, a mineralocorticoid receptor mediated biological activity in another tissue type.

The term "monitoring" refers to observing an effect or absence of any effect. In certain embodiments, one monitors cells after contacting those cells with a compound of the present invention. Examples of effects that may be monitored include, but are not limited to, changes in cell phenotype, cell proliferation, a mineralocorticoid receptor activity, or the interaction between a mineralocorticoid receptor and a natural binding partner.

The term "cell phenotype" refers to physical or biological characteristics. Examples of characteristics that constitute phenotype included, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

The term "cell proliferation" refers to the rate at which cells divide. The number of cells growing in a vessel can be quantified by a person skilled in the art (e.g., by counting cells in a defined area using a light microscope, or by using laboratory apparatus that measure the density of cells in an appropriate medium). One skilled in that art can calculate cell proliferation by determining the number of cells at two or more times.

The term "contacting" refers to bringing two or more materials into close enough proximity that they may interact. In certain embodiments, contacting can be accomplished in a vessel such as a test tube, a Petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may dead. Cells may or may not be intact.

Certain Compounds

Certain compounds that bind to mineralocorticoid receptors and/or certain compounds that modulate an activity of such receptors play a role in health (e.g., normal growth, development, and/or absence of disease). In certain embodiments, compounds of the present invention are useful for treating any of a variety of diseases or conditions.

Certain compounds have been previously described as receptor modulators or as possible receptor modulators. See e.g. U.S. Pat. Nos. 6,462,038, 5,693,646; 6,380,207; 6,506, 766; 5,688,810; 5,696,133; 6,569,896, 6,673,799; 4,636,505; 4,097,578; 3,847,988; U.S. application Ser. No. 10/209,461 (Pub. No. US 2003/0055094); WO 01/27086; WO 02/22585; Zhi, et al. *Bioorganic & Medicinal Chemistry Letters* 2000, 10, 415-418; Pooley, et. al., *J. Med. Chem.* 1998, 41, 3461; Hamann, et al. *J. Med. Chem.* 1998, 41(4), 623; and Yin, et al., *Molecular Pharmacology*, 2003, 63 (1), 211-223 the entire disclosures of which are incorporated in their entirety. Certain cyclothiocarbamate analogues have been described as progesterone receptor modulators (e.g., U.S. Pat. No. 6,436, 929 and U.S. Pat. No. 6,509,334). Certain cyclocarbamate analogues have been described as progesterone receptor antagonists (e.g., U.S. Pat. No. 6,306,851, U.S. Pat. No. 6,380,178, U.S. Pat. No. 6,441,019, U.S. Pat. No. 6,444,668, U.S. Pat. No. 6,509,334, and U.S. Pat. No. 6,566,358; Zhang, P. et al. *J. Med. Chem.* 45:4379 (2002)).

In certain embodiments, the present invention provides selective mineralocorticoid receptor modulators. In certain embodiments, the invention provides selective mineralocorticoid receptor binding agents. In certain embodiments, the invention provides methods of making and methods of using selective mineralocorticoid receptor modulators and/or selective mineralocorticoid binding agents. In certain embodiments, selective mineralocorticoid modulators are agonists, partial agonists, and/or antagonists for the mineralocorticoid receptor.

In certain embodiments, the present invention provides a compound of Formula I:

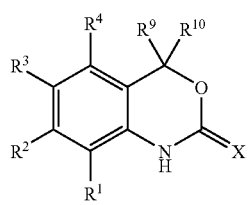

(I)

or a pharmaceutically acceptable salt, ester, amide, or prodrug thereof.

In certain embodiments, $R^1$ is selected from the group consisting of hydrogen, a halogen, CN, $OR^{16}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^1$ is an optionally substituted $C_1$-$C_8$ alkyl or an optionally substituted $C_3$-$C_8$ cycloalkyl that is fully saturated. In certain embodiments, $R^1$ is an optionally substituted $C_1$-$C_8$ alkyl or an optionally substituted $C_3$-$C_8$ cycloalkyl that is not fully saturated. In certain such embodiments, $R^1$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^1$ is selected from the group consisting of an optionally substituted methyl, ethyl propyl isopropyl, butyl, sec-butyl, and tert-butyl. In certain embodiments, $R^1$ is methyl. In certain embodiments, $R^1$ is trifluoromethyl. In certain of the embodiments where $R^1$ is a halogen, $R^1$ is F or Cl.

In certain embodiments, $R^2$ is selected from the group consisting of hydrogen, a halogen, CN, $OR^{16}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^2$ is an optionally substituted $C_1$-$C_8$ alkyl or an optionally substituted $C_3$-$C_8$ cycloalkyl that is fully saturated. In certain embodiments, $R^2$ is an optionally substituted $C_1$-$C_8$ alkyl or an optionally substituted $C_3$-$C_8$ cycloalkyl that is not fully saturated. In certain such embodiments, $R^2$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^2$ is selected from the group consisting of an optionally substituted methyl, ethyl propyl isopropyl, butyl, sec-butyl, and tert-butyl. In certain embodiments, $R^2$ is methyl. In certain embodiments, $R^2$ is trifluoromethyl. In certain of the embodiments where $R^2$ is a halogen, $R^2$ is F or Cl.

In certain embodiments, $R^4$ is selected from the group consisting of hydrogen, a halogen, $NO_2$, $OR^9$, $NR^{10}R^{11}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^4$ is an optionally substituted $C_1$-$C_8$ alkyl or an optionally substituted $C_3$-$C_8$ cycloalkyl that is fully saturated. In certain embodiments, $R^4$ is an optionally substituted $C_1$-$C_8$ alkyl or an optionally substituted $C_3$-$C_8$ cycloalkyl that is not fully saturated. In certain such embodiments, $R^4$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^4$ is selected from the group consisting of an optionally substituted methyl, ethyl propyl isopropyl, butyl, sec-butyl, and tert-butyl. In certain embodiments, $R^4$ is methyl. In certain embodiments, $R^4$ is trifluoromethyl. In certain of the embodiments where $R^4$ is a halogen, $R^4$ is selected from the group consisting of F, Cl, Br, and I.

In certain embodiments, $R^9$ is selected from the group consisting of hydrogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^9$ is an optionally substituted $C_1$-$C_8$ alkyl or an optionally substituted $C_3$-$C_8$ cycloalkyl that is fully saturated. In certain embodiments, $R^9$ is an optionally substituted $C_1$-$C_8$ alkyl or an optionally substituted $C_3$-$C_8$ cycloalkyl that is not fully saturated. In certain such embodiments, $R^9$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^9$ is selected from the group consisting of an optionally substituted methyl, ethyl propyl isopropyl, butyl, sec-butyl, and tert-butyl. In certain embodiments, $R^9$ is methyl. In certain embodiments, $R^9$ is trifluoromethyl.

In certain embodiments, $R^{10}$ is selected from the group consisting of hydrogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{10}$ is an optionally substituted $C_1$-$C_8$ alkyl or an optionally substituted $C_3$-$C_8$ cycloalkyl that is fully saturated. In certain embodiments, $R^{10}$ is an optionally substituted $C_1$-$C_8$ alkyl or an optionally substituted $C_3$-$C_8$ cycloalkyl that is not fully saturated. In certain such embodiments, $R^{10}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{10}$ is selected from the group consisting of an optionally substituted methyl, ethyl propyl isopropyl, butyl, sec-butyl, and tert-butyl. In certain embodiments, $R^{10}$ is methyl. In certain embodiments, $R^{10}$ is trifluoromethyl.

In certain embodiments, X is selected from the group consisting of O, S, and $NOR^{16}$.

In certain embodiments, $R^3$ is selected from the group consisting of (a), (b), (c), (d), (e), (f), (g), (h), (i), and (j):

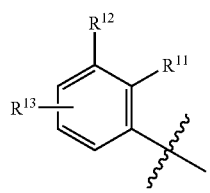

(a)

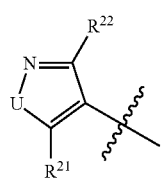

(b)

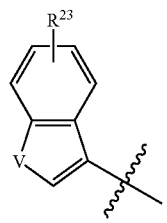

(c)

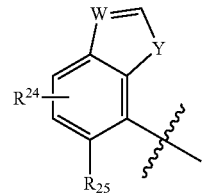

(d)

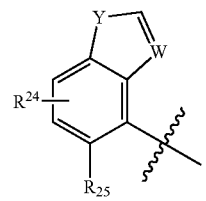

(e)

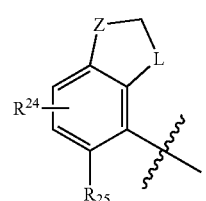

(f)

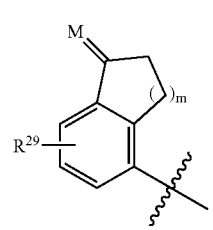

(g)

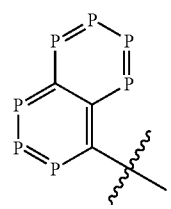

(h)

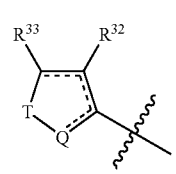

(i)

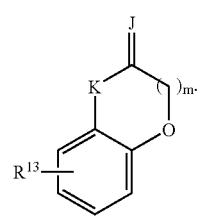

(j)

In certain embodiments, $R^{11}$ is selected from the group consisting of hydrogen, a halogen, CN, $OR^{16}$, $NR^{17}R^{18}$, $CH_2R^{16}$, $COR^{20}$, $CO_2R^{20}$, $CONR^{20}R^{20}$, $SOR^{20}$, or $SO_2R^{20}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{11}$ is an optionally substituted $C_1$-$C_8$ alkyl or an optionally substituted $C_3$-$C_8$ cycloalkyl that is fully saturated. In certain embodiments, $R^{11}$ is an optionally substituted $C_1$-$C_8$ alkyl or an optionally substituted $C_3$-$C_8$ cycloalkyl that is not fully saturated. In certain such embodiments, $R^{11}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{11}$ is selected from the group consisting of an optionally substituted methyl, ethyl propyl isopropyl, butyl, sec-butyl, and tert-butyl. In certain embodiments, $R^{11}$ is methyl. In certain embodiments, $R^{11}$ is trifluoromethyl. In certain of the embodiments where $R^{11}$ is a halogen, $R^{11}$ is F or Cl.

In certain embodiments, $R^{12}$ is selected from the group consisting of hydrogen, a halogen, CN, $COR^{20}$, $CO_2R^{20}$, $CONR^{20}R^{20}$, $SOR^{20}$, $SO_2R^{20}$, $NO_2$, $OR^{16}$, $NR^{17}R^{18}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{12}$ is an optionally substituted $C_1$-$C_8$ alkyl or an optionally substituted $C_3$-$C_8$ cycloalkyl that is fully saturated. In certain embodiments, $R^{12}$ is an optionally substituted $C_1$-$C_8$ alkyl or an optionally substituted $C_3$-$C_8$ cycloalkyl that is not fully saturated. In certain such embodiments, $R^{12}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{12}$ is selected from the group consisting of an optionally substituted methyl, ethyl propyl isopropyl, butyl, sec-butyl, and tert-butyl. In certain embodiments, $R^{12}$ is methyl. In certain embodiments, $R^{12}$ is trifluoromethyl. In certain of the embodiments where $R^{12}$ is a halogen, $R^{12}$ is F or Cl.

In certain embodiments, $R^{13}$ is selected form hydrogen, a halogen, CN, $OR^{16}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{13}$ is an optionally substituted $C_1$-$C_8$ alkyl or an optionally substituted $C_3$-$C_8$ cycloalkyl that is fully saturated. In certain embodiments, $R^{13}$ is an optionally substituted $C_1$-$C_8$ alkyl or an optionally substituted $C_3$-$C_8$ cycloalkyl that is not fully saturated. In certain such embodiments, $R^{13}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{13}$ is selected from the group consisting of an optionally substituted methyl, ethyl propyl isopropyl, butyl, sec-butyl, and tert-butyl. In certain embodiments, $R^{13}$ is methyl. In certain embodiments, $R^{13}$ is trifluoromethyl. In certain of the embodiments where $R^{13}$ is a halogen, $R^{13}$ is F or Cl.

In certain embodiments, $R^{21}$ is selected from the group consisting of hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{21}$ is an optionally substituted $C_1$-$C_8$ alkyl or an optionally substituted $C_3$-$C_8$ cycloalkyl that is fully saturated. In certain embodiments, $R^{21}$ is an optionally substituted $C_1$-$C_8$ alkyl or an optionally substituted $C_3$-$C_8$ cycloalkyl that is not fully saturated. In certain such embodiments, $R^{21}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{21}$ is selected from the group consisting of an optionally substituted methyl, ethyl propyl isopropyl, butyl, sec-butyl, and tert-butyl. In certain embodiments, $R^{21}$ is methyl. In certain embodiments, $R^{21}$ is trifluoromethyl. In certain of the embodiments where $R^{21}$ is a halogen, $R^{21}$ is F or Cl.

In certain embodiments, $R^{22}$ is selected from the group consisting of hydrogen, a halogen, $OR^{16}$, $NR^{17}R^{18}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{22}$ is an optionally substituted $C_1$-$C_8$ alkyl or an optionally substituted $C_3$-$C_8$ cycloalkyl that is fully saturated. In certain embodiments, $R^{22}$ is an optionally substituted $C_1$-$C_8$ alkyl or an optionally substituted $C_3$-$C_8$ cycloalkyl that is not fully saturated. In certain such embodiments, $R^{22}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{22}$ is selected from the group consisting of an optionally substituted methyl, ethyl propyl isopropyl, butyl, sec-butyl, and tert-butyl. In certain embodiments, $R^{22}$ is methyl. In certain embodiments, $R^{22}$ is trifluoromethyl. In certain of the embodiments where $R^{22}$ is a halogen, $R^{22}$ is F or Cl.

In certain embodiments, $R^{23}$ is selected from the group consisting of hydrogen, a halogen, $OR^{16}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{23}$ is an optionally substituted $C_1$-$C_8$ alkyl or an optionally substituted $C_3$-$C_8$ cycloalkyl that is fully saturated. In certain embodiments, $R^{23}$ is an optionally substituted $C_1$-$C_8$ alkyl or an optionally substituted $C_3$-$C_8$ cycloalkyl that is not fully saturated. In certain such embodiments, $R^{23}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{23}$ is selected from the group consisting of an optionally substituted methyl, ethyl propyl isopropyl, butyl, sec-butyl, and tert-butyl. In certain embodiments, $R^{23}$ is methyl. In certain embodiments, $R^{23}$ is trifluoromethyl. In certain of the embodiments where $R^{23}$ is a halogen, $R^{23}$ is F or Cl.

In certain embodiments, $R^{24}$ is selected from the group consisting of hydrogen, a halogen, CN, $OR^{16}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{24}$ is an optionally substituted $C_1$-$C_8$ alkyl or an optionally substituted $C_3$-$C_8$ cycloalkyl that is fully saturated. In certain embodiments, $R^{24}$ is an optionally substituted $C_1$-$C_8$ alkyl or an optionally substituted $C_3$-$C_8$ cycloalkyl that is not fully saturated. In certain such embodiments, $R^{24}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{24}$ is selected from the group consisting of an optionally substituted methyl, ethyl propyl isopropyl, butyl, sec-butyl, and tert-butyl. In certain embodiments, $R^{24}$ is methyl. In certain embodiments, $R^{24}$ is trifluoromethyl. In certain of the embodiments where $R^{24}$ is a halogen, $R^{24}$ is F or Cl.

In certain embodiments, $R^{25}$ is selected from the group consisting of hydrogen, a halogen, CN, $OR^{16}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{25}$ is an optionally substituted $C_1$-$C_8$ alkyl or an optionally substituted $C_3$-$C_8$ cycloalkyl that is fully saturated. In certain embodiments, $R^{25}$ is an optionally substituted $C_1$-$C_8$ alkyl or an optionally substituted $C_3$-$C_8$ cycloalkyl that is not fully saturated. In certain such embodiments, $R^{25}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{25}$ is selected from the group consisting of an optionally substituted methyl, ethyl propyl isopropyl, butyl, sec-butyl, and tert-butyl. In certain embodiments, $R^{25}$ is methyl. In certain embodiments, $R^{25}$ is trifluoromethyl. In certain of the embodiments where $R^{25}$ is a halogen, $R^{25}$ is F or Cl.

In certain embodiments, $R^{29}$ is selected from the group consisting of hydrogen, a halogen, CN, $OR^{16}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{29}$ is an optionally substituted $C_1$-$C_8$ alkyl or an optionally substituted $C_3$-$C_8$ cycloalkyl that is fully saturated. In certain embodiments, $R^{29}$ is an optionally substituted $C_1$-$C_8$ alkyl or an optionally substituted $C_3$-$C_8$ cycloalkyl that is not fully saturated. In certain such embodiments, $R^{29}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{29}$ is selected from the group consisting of an optionally substituted methyl, ethyl propyl isopropyl, butyl, sec-butyl, and tert-butyl. In certain embodiments, $R^{29}$ is methyl. In certain embodiments, $R^{29}$ is trifluoromethyl. In certain of the embodiments where $R^{29}$ is a halogen, $R^{29}$ is F or Cl.

In certain embodiments, $R^{32}$ is selected from the group consisting of hydrogen, a halogen, CN, $OR^{16}$, $COR^{20}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{32}$ is an optionally substituted $C_1$-$C_8$ alkyl or an optionally substituted $C_3$-$C_8$ cycloalkyl that is fully saturated. In certain embodiments, $R^{32}$ is an optionally substituted $C_1$-$C_8$ alkyl or an optionally substituted $C_3$-$C_8$ cycloalkyl that is not fully saturated. In certain such embodiments, $R^{32}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{32}$ is selected from the group consisting of an optionally substituted methyl, ethyl propyl isopropyl, butyl, sec-butyl, and tert-butyl. In certain embodiments, $R^{32}$ is methyl. In certain embodiments, $R^{29}$ is trifluoromethyl. In certain of the embodiments where $R^{32}$ is a halogen, $R^{32}$ is F or Cl.

In certain embodiments, $R^{33}$ is selected from the group consisting of hydrogen, a halogen, CN, $OR^{16}$, $COR^{20}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{33}$ is an optionally substituted $C_1$-$C_8$ alkyl or an optionally substituted $C_3$-$C_8$ cycloalkyl that is fully saturated. In certain embodiments, $R^{33}$ is an optionally substituted $C_1$-$C_8$ alkyl or an optionally substituted $C_3$-$C_8$ cycloalkyl that is not fully saturated. In certain such embodiments, $R^{33}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{33}$ is selected from the group consisting of an optionally substituted methyl, ethyl propyl isopropyl, butyl, sec-butyl, and tert-butyl. In certain embodiments, $R^{33}$ is methyl. In certain embodiments, $R^{33}$ is trifluoromethyl. In certain of the embodiments where $R^{33}$ is a halogen, $R^{33}$ is F or Cl.

In certain embodiments, $R^{16}$ is selected from the group consisting of hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{16}$ is an optionally substituted $C_1$-$C_8$ alkyl or an optionally substituted $C_3$-$C_8$ cycloalkyl that is fully saturated. In certain embodiments, $R^{16}$ is an optionally substituted $C_1$-$C_8$ alkyl or an optionally substituted $C_3$-$C_8$ cycloalkyl that is not fully saturated. In certain such embodiments, $R^{16}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{16}$ is selected from the group consisting of an optionally substituted methyl, ethyl propyl isopropyl, butyl, sec-butyl, and tert-butyl. In certain embodiments, $R^{16}$ is methyl. In certain embodiments, $R^{16}$ is trifluoromethyl. In certain of the embodiments where $R^{16}$ is a halogen, $R^{16}$ is F or Cl.

In certain embodiments, $R^{17}$ is selected from the group consisting of hydrogen, a halogen, $COR^{20}$, $CO_2R^{20}$, $SO_2R^{20}$, $S(O)R^{20}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{17}$ is an optionally substituted $C_1$-$C_8$ alkyl or an optionally substituted $C_3$-$C_8$ cycloalkyl that is fully saturated. In certain embodiments, $R^{17}$ is an optionally substituted $C_1$-$C_8$ alkyl or an optionally substituted $C_3$-$C_8$ cycloalkyl that is not fully saturated. In certain such embodiments, $R^{17}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{17}$ is selected from the group consisting of an optionally substituted methyl, ethyl propyl isopropyl, butyl, sec-butyl, and tert-butyl. In certain embodiments, $R^{17}$ is methyl. In certain embodiments, $R^{17}$ is trifluoromethyl. In certain of the embodiments where $R^{17}$ is a halogen, $R^{17}$ is F or Cl.

In certain embodiments, $R^{18}$ is selected from the group consisting of hydrogen, a halogen, $COR^{20}$, $CO_2R^{20}$, $SO_2R^{20}$, $S(O)R^{20}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{18}$ is an optionally substituted $C_1$-$C_8$ alkyl or an optionally substituted $C_3$-$C_8$ cycloalkyl that is fully saturated. In certain embodiments, $R^{18}$ is an optionally substituted $C_1$-$C_8$ alkyl or an optionally substituted $C_3$-$C_8$ cycloalkyl that is not fully saturated. In certain such embodiments, $R^{18}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{18}$ is selected from the group consisting of an optionally substituted methyl, ethyl propyl isopropyl, butyl, sec-butyl, and tert-butyl. In certain embodiments, $R^{18}$ is methyl. In certain embodiments, $R^{18}$ is trifluoromethyl. In certain of the embodiments where $R^{18}$ is a halogen, $R^{18}$ is F or Cl.

In certain embodiments, $R^{20}$ is selected from the group consisting of hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{20}$ is an optionally substituted $C_1$-$C_8$ alkyl or an optionally substituted $C_3$-$C_8$ cycloalkyl that is fully saturated. In certain embodiments, $R^{20}$ is an optionally substituted $C_1$-$C_8$ alkyl or an optionally substituted $C_3$-$C_8$ cycloalkyl that is not fully saturated. In certain such embodiments, $R^{20}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{20}$ is selected from the group consisting of an optionally substituted methyl, ethyl propyl isopropyl, butyl, sec-butyl, and tert-butyl. In certain embodiments, $R^{20}$ is methyl. In certain embodiments, $R^{20}$ is trifluoromethyl. In certain of the embodiments where $R^{20}$ is a halogen, $R^{20}$ is F or Cl.

In certain embodiments, $R^{26}$ is selected from the group consisting of hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{26}$ is an optionally substituted $C_1$-$C_8$ alkyl or an optionally substituted $C_3$-$C_8$ cycloalkyl that is fully saturated. In certain embodiments, $R^{26}$ is an optionally substituted $C_1$-$C_8$ alkyl or an optionally substituted $C_3$-$C_8$ cycloalkyl that is not fully saturated. In certain such embodiments, $R^{26}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{26}$ is selected from the group consisting of an optionally substituted methyl, ethyl propyl isopropyl, butyl, sec-butyl, and tert-butyl. In certain embodiments, $R^{26}$ is methyl. In certain embodiments, $R^{26}$ is trifluoromethyl. In certain of the embodiments where $R^{26}$ is a halogen, $R^{26}$ is F or Cl.

In certain embodiments, $R^{27}$ is selected from the group consisting of hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{27}$ is an optionally substituted $C_1$-$C_8$ alkyl or an optionally substituted $C_3$-$C_8$ cycloalkyl that is fully saturated. In certain embodiments, $R^{27}$ is an optionally substituted $C_1$-$C_8$ alkyl or an optionally substituted $C_3$-$C_8$ cycloalkyl that is not fully saturated. In certain such embodiments, $R^{27}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{27}$ is selected from the group consisting of an optionally substituted methyl, ethyl propyl isopropyl, butyl, sec-butyl, and tert-butyl. In certain embodiments, $R^{27}$ is methyl. In certain embodiments, $R^{27}$ is trifluoromethyl. In certain of the embodiments where $R^{27}$ is a halogen, $R^{27}$ is selected from the group consisting of F, Cl, and Br.

In certain embodiments, $R^{28}$ is selected from the group consisting of hydrogen, a halogen, $COR^{20}$, $CO_2R^{20}$, $CONR^{20}$, $SO_2R^{20}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{28}$ is an optionally substituted $C_1$-$C_8$ alkyl or an optionally substituted $C_3$-$C_8$ cycloalkyl that is fully saturated. In certain embodiments, $R^{28}$ is an optionally substituted $C_1$-$C_8$ alkyl or an optionally substituted $C_3$-$C_8$ cycloalkyl that is not fully saturated. In certain such embodiments, $R^{28}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{28}$ is selected from the group consisting of an optionally substituted methyl, ethyl propyl isopropyl, butyl, sec-butyl, and tert-butyl. In certain embodiments, $R^{28}$ is methyl. In certain embodiments, $R^{28}$ is trifluoromethyl. In certain of the embodiments where $R^{28}$ is a halogen, $R^{28}$ is F or Cl.

In certain embodiments, $R^{30}$ is selected from the group consisting of hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{30}$ is an optionally substituted $C_1$-$C_8$ alkyl or an optionally substituted $C_3$-$C_8$ cycloalkyl that is fully saturated. In certain embodiments, $R^{30}$ is an optionally substituted $C_1$-$C_8$ alkyl or an optionally substituted $C_3$-$C_8$ cycloalkyl that is not fully saturated. In certain such embodiments, $R^{30}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{30}$ is selected from the group consisting of an optionally substituted methyl, ethyl propyl isopropyl, butyl, sec-butyl, and tert-butyl. In certain embodiments, $R^{30}$ is methyl. In certain embodiments, $R^{30}$ is trifluoromethyl. In certain of the embodiments where $R^{30}$ is a halogen, $R^{30}$ is F or Cl.

In certain embodiments, $R^{31}$ is selected from the group consisting of hydrogen, a halogen, $OR^{16}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{31}$ is an optionally substituted $C_1$-$C_8$ alkyl or an optionally substituted $C_3$-$C_8$ cycloalkyl that is fully saturated. In certain embodiments, $R^{31}$ is an optionally substituted $C_1$-$C_8$ alkyl or an optionally substituted $C_3$-$C_8$ cycloalkyl that is not fully saturated. In certain such embodiments, $R^{31}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{31}$ is selected from the group consisting of an optionally substituted methyl, ethyl propyl isopropyl, butyl, sec-butyl, and tert-butyl. In certain embodiments, $R^{31}$ is methyl. In certain embodiments, $R^{31}$ is trifluoromethyl. In certain of the embodiments where $R^{31}$ is a halogen, $R^{31}$ is F or Cl.

In certain embodiments, $R^{34}$ is selected from the group consisting of hydrogen, a halogen, $NO_2$, $OR^{16}$, $NR^{17}R^{18}$, CN, $COR^{20}$, $COR^{20}$, $CO_2R^{20}$, $SO_2R^{20}$, $S(O)R^{20}$, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{34}$ is an optionally substituted $C_1$-$C_8$ alkyl or an optionally substituted $C_3$-$C_8$ cycloalkyl that is fully saturated. In certain embodiments, $R^{34}$ is an optionally substituted $C_1$-$C_8$ alkyl or an optionally substituted $C_3$-$C_8$ cycloalkyl that is not fully saturated. In certain such embodiments, $R^{34}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{34}$ is selected from the group consisting of an optionally substituted methyl, ethyl propyl isopropyl, butyl, sec-butyl, and tert-butyl. In certain embodiments, $R^{34}$ is methyl. In certain embodiments, $R^{34}$ is trifluoromethyl. In certain of the embodiments where $R^{34}$ is a halogen, $R^{34}$ is F or Cl.

In certain embodiments, $R^{35}$ is selected from the group consisting of hydrogen, a halogen, an optionally substituted $C_1$-$C_6$ alkyl, an optionally substituted $C_1$-$C_6$ heteroalkyl, an optionally substituted $C_1$-$C_6$ haloalkyl, an optionally substituted $C_1$-$C_6$ heterohaloalkyl, an optionally substituted $C_3$-$C_8$ cycloalkyl, an optionally substituted $C_2$-$C_8$ heterocycle, an optionally substituted an optionally substituted $C_5$-$C_8$ aryl, and an optionally substituted an optionally substituted $C_3$-$C_8$ heteroaryl. In certain embodiments, $R^{35}$ is an optionally substituted $C_1$-$C_8$ alkyl or an optionally substituted $C_3$-$C_8$ cycloalkyl that is fully saturated. In certain embodiments, $R^{35}$ is an optionally substituted $C_1$-$C_8$ alkyl or an optionally substituted $C_3$-$C_8$ cycloalkyl that is not fully saturated. In certain such embodiments, $R^{35}$ is selected from the group consisting of an optionally substituted $C_2$-$C_8$ alkenyl, an optionally substituted $C_2$-$C_8$ alkynyl, an optionally substituted $C_3$-$C_8$ cycloalkenyl, and an optionally substituted $C_3$-$C_8$ cycloalkynyl. In certain of the embodiments, $R^{35}$ is selected from the group consisting of an optionally substituted methyl, ethyl propyl isopropyl, butyl, sec-butyl, and tert-butyl. In certain embodiments, $R^{35}$ is methyl. In certain embodiments, $R^{35}$ is trifluoromethyl. In certain of the embodiments where $R^{35}$ is a halogen, $R^{35}$ is F or Cl.

In certain embodiments, J is selected from the group consisting of O and S.

In certain embodiments, K is selected from the group consisting of O and $NR^{35}$.

In certain embodiments, M is selected from the group consisting of O and $NOR^{30}$.

In certain embodiments, m is selected from 0, 1, 2, and 3.

In certain embodiments, each P is independently selected from the group consisting of N and $CR^{31}$. In certain embodiments, at least one P is N. In certain embodiments, at least two Ps are N. In certain embodiments, at least three Ps are N. In certain embodiments, no more than 3 Ps are N. In certain embodiments, no more than 2 Ps are N. In certain embodiments, no more than one P is N. In certain embodiments, one P is N. In certain embodiments, two Ps are N. In certain embodiments, three Ps are N.

In certain embodiments, Q is selected from the group consisting of S, O, $NR^{17}$, and $CR^{34}$.

In certain embodiments, T is selected from the group consisting of S, O, $NR^{17}$, and $CR^{34}$.

In certain embodiments, either Q is $CR^{34}$ and T is selected from the group consisting of S, O $NR^{17}$ or T is $CR^{34}$ and Q is selected from the group consisting of S, O $NR^{17}$.

In certain embodiments, U is selected from the group consisting of O and $NR^{17}$.

In certain embodiments, V is selected from the group consisting of O, S, and $NR^{17}$.

In certain embodiments, W is selected from the group consisting of $CR^{27}$ and N.

In certain embodiments, X is selected from the group consisting of O, S, and $NOR^{16}$.

In certain embodiments, Y is selected from the group consisting of $NR^{26}$, S and O.

In certain embodiments, Z is selected from the group consisting of $NR^{28}$, O, and an optionally substituted alkyl. In certain embodiments, L is selected from the group consisting of $NR^{28}$, O, and an optionally substituted alkyl. In certain embodiments, either Z is $CH_2$ and L is selected from the group consisting of $NR^{28}$ and O, or L is $CH_2$ and Z is selected from the group consisting of $NR^{28}$ and O.

In certain embodiments, m is selected from 0, 1, and 2.

In certain embodiments, n is selected from 0, 1, and 2.

In certain embodiments, at least one of $R^1$, $R^2$ or $R^4$ is not hydrogen. In certain embodiments, at least two of $R^1$, $R^2$ or $R^4$ are not hydrogen. In certain embodiments, if one of $R^1$, $R^2$ or $R^4$ is hydrogen, then at least one of the other two of those groups is not methyl.

In embodiments in which two or more of a particular group are present, the identities of those two or more particular groups are selected independently and, thus, may be the same or different from one another. For example, certain compounds of the invention comprise two or more $R^{16}$ groups. The identities of those two or more $R^{16}$ groups are each selected independently. Thus, in certain embodiments, those $R^{16}$ groups are all the same as one another; in certain embodiments, those $R^{16}$ groups are all different from one another; and in certain embodiments, some of those $R^{16}$ groups are the same as one another and some are different from one another. This independent selection applies to any group that is present in a compound more than once.

In certain embodiments, a compound of Formula I is a selective mineralocorticoid receptor modulator. In certain embodiments, a compound of Formula I is a selective mineralocorticoid receptor agonist. In certain embodiments, a compound of Formula I is a selective mineralocorticoid receptor antagonist. In certain embodiments, a compound of Formula I is a selective mineralocorticoid receptor partial agonist. In certain embodiments, a compound of Formula I is a tissue-specific selective mineralocorticoid receptor modulator. In certain embodiments, a compound of Formula I is a gene-specific selective mineralocorticoid receptor modulator. In certain embodiments, a compound of Formula I is a selective mineralocorticoid receptor binding compound.

In certain embodiments, the invention provides compounds selected from the group consisting of:

5-Chloro-6-(3-cyanophenyl)-1,4-dihydro-4,4-dimethyl-2H-3,1-benzoxazin-2-one (Compound 101);

5-Chloro-1,4-dihydro-4,4-dimethyl-6-[3-(trifluoromethyl)phenyl]-2H-3,1-benzoxazin-2-one (Compound 102);

6-(3-Acetylphenyl)-5-chloro-1,4-dihydro-4,4-dimethyl-2H-3,1-benzoxazin-2-one (Compound 103);

5-Chloro-1,4-dihydro-4,4-dimethyl-6-[3-(trifluoromethyl)phenyl]-2H-3,1-benzoxazin-2-thione (Compound 104);

5-Chloro-6-(3-chlorophenyl)-1,4-dihydro-4,4-dimethyl-2H-3,1-benzoxazin-2-one (Compound 105);

5-Chloro-6-(3-cyanophenyl)-1,4-dihydro-4,4-dimethyl-2H-3,1-benzoxazin-2-thione (Compound 106);

6-(3-Carboxymethylphenyl)-5-chloro-1,4-dihydro-4,4-dimethyl-2H-3,1-benzoxazin-2-one (Compound 107);

5-Chloro-6-(3-cyanophenyl)-1,4-dihydro-1,4,4-trimethyl-2H-3,1-benzoxazin-2-one (Compound 108);

5-Chloro-6-(3-cyano-2-methoxyphenyl)-1,4-dihydro-4,4-dimethyl-2H-3,1-benzoxazin-2-one (Compound 109);

(±)-5-Chloro-1,4-dihydro-4-methyl-6-[3-(trifluoromethyl)phenyl]-2H-3,1-benzoxazin-2-one (Compound 110);

(±)-5-Chloro-1,4-dihydro-4-methyl-6-[3-(trifluoromethyl)phenyl]-2H-3,1-benzoxazin-2-thione (Compound 111);

(±)-5-Chloro-6-(3-cyanophenyl)-4-ethyl-1,4-dihydro-2H-3,1-benzoxazin-2-one (Compound 112);

(±)-5-Chloro-6-(3-cyanophenyl)-4-ethyl-1,4-dihydro-2H-3,1-benzoxazin-2-thione (Compound 113);

(±)-5-Chloro-6-(3-cyanophenyl)-4-(4-fluorophenyl)-1,4-dihydro-2H-3,1-benzoxazin-2-one (Compound 114);

(±)-5-Chloro-4-ethyl-1,4-dihydro-6-[3-(trifluoromethyl)phenyl]-2H-3,1-benzoxazin-2-one (Compound 115);

(±)-5-Chloro-6-(3-cyanophenyl)-4-(4-fluorophenyl)-1,4-dihydro-2H-3,1-benzoxazin-2-thione (Compound 116);

(±)-5-Chloro-4-ethyl-1,4-dihydro-6-[3-(trifluoromethyl)phenyl]-2H-3,1-benzoxazin-2-thione (Compound 117);

(±)-5-Chloro-4-(4-fluorophenyl)-1,4-dihydro-6-[3-(trifluoromethyl)phenyl]-2H-3,1-benzoxazin-2-one (Compound 118);

(±)-5-Chloro-6-(3-cyanophenyl)-4-cyclopentyl-1,4-dihydro-2H-3,1-benzoxazin-2-one (Compound 119);

(±)-5-Chloro-6-(3-cyanophenyl)-4-cyclopentyl-1,4-dihydro-2H-3,1-benzoxazin-2-thione (Compound 120);

(±)-5-Chloro-6-(3-cyanophenyl)-4-(3,4-difluorobenzyl)-1,4-dihydro-2H-3,1-benzoxazin-2-one (Compound 121);

(±)-5-Chloro-6-(3-cyanophenyl)-4-(3,4-difluorobenzyl)-1,4-dihydro-2H-3,1-benzoxazin-2-thione (Compound 122);

5-Chloro-1,4-dihydro-6-(2,6-dimethoxyphenyl)-4,4-dimethyl-2H-3,1-benzoxazin-2-one (Compound 123);

7-Chloro-6-(3-cyanophenyl)-1,4-dihydro-4,4-dimethyl-2H-3,1-benzoxazin-2-one (Compound 124);

7-Chloro-6-(3-cyanophenyl)-1,4-dihydro-4,4-dimethyl-2H-3,1-benzoxazin-2-thione (Compound 125);

7-Chloro-6-(3-cyano-2-methoxyphenyl)-1,4-dihydro-4,4-dimethyl-2H-3,1-benzoxazin-2-one (Compound 126);

7-Chloro-6-(3-cyano-2-methoxyphenyl)-1,4-dihydro-4,4-dimethyl-2H-3,1-benzoxazin-2-thione (Compound 127);

6-(3,5-Dimethylisoxazol-4-yl)-1,4-dihydro-4,4,8-trimethyl-2H-3,1-benzoxazin-2-one (Compound 128);

1,4-Dihydro-6-(indol-7-yl)-4,4,8-trimethyl-2H-3,1-benzoxazin-2-one (Compound 129);

and a pharmaceutically acceptable salt, ester, amide, or prodrug of any of those compounds.

Certain compounds of the present inventions may exist as stereoisomers including optical isomers. The present disclosure is intended to include all stereoisomers and both the racemic mixtures of such stereoisomers as well as the individual enantiomers that may be separated according to methods that are known in the art or that may be excluded by synthesis schemes known in the art designed to yield predominantly one enantiomer relative to another.

Certain Synthesis Methods

Certain synthesis schemes are now provided. The synthesis schemes are provide only to illustrate possible ways to make certain compounds of the invention and do not limit the invention in any way. One of skill in the art will recognize that compounds of the present invention may be synthesized through any of a variety of schemes using a variety of different starting materials.

In certain embodiments, synthesis of 6-aryl- and 6-heteroaryl 2H-3,1-benzoxazine-2-one (e.g. Structure 6) and 6-aryl- and 6-heteroaryl 2H-3,1-benzoxazine-2-thiones (Structure 8) is accomplished using Scheme I.

Scheme I

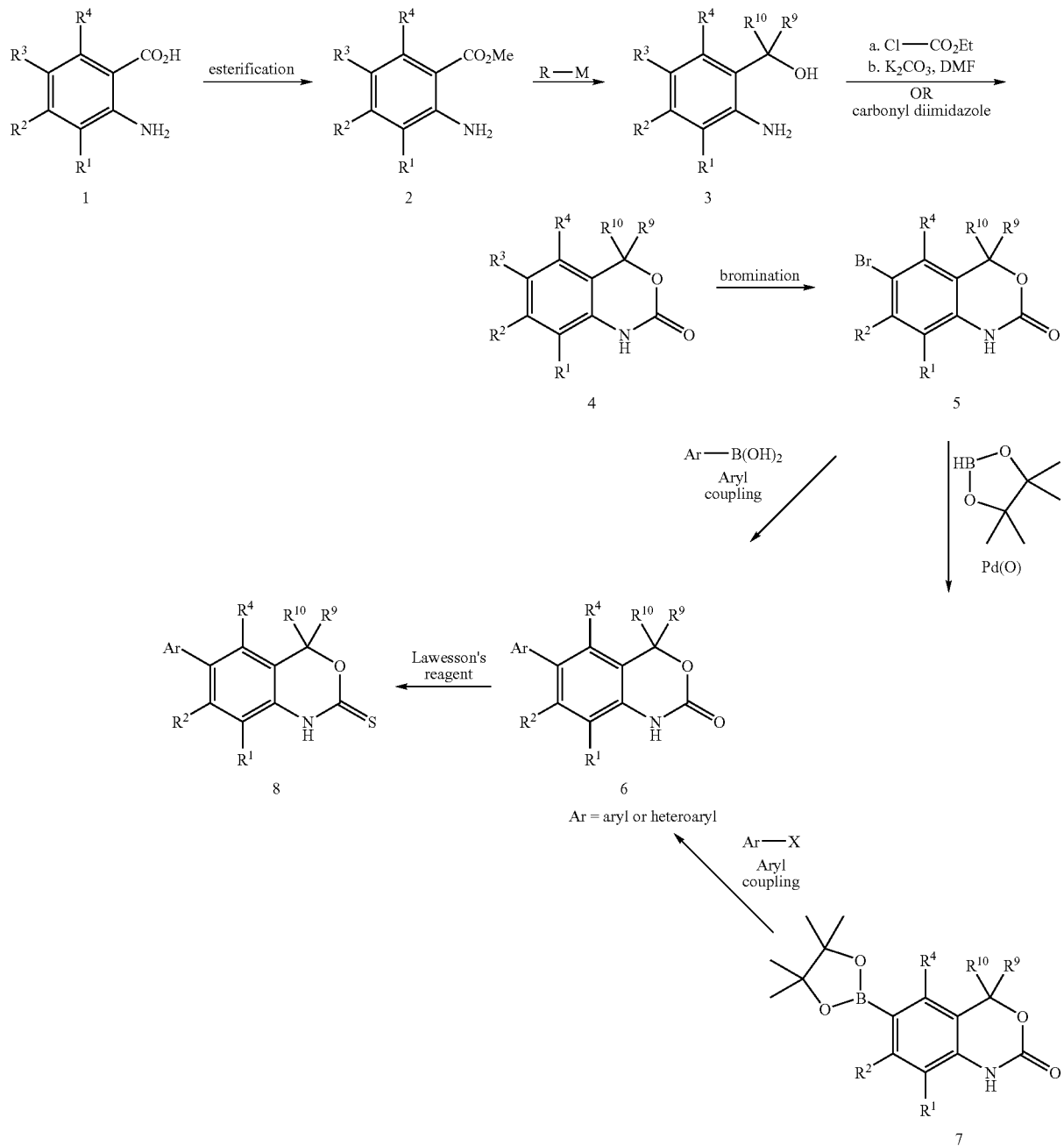

Ar = aryl or heteroaryl

The process of Scheme I begins with the esterification of an aminobenzoic acid derivative (Structure 1), with an esterification reagent, for example, trimethylsilyldiazomethane in benzene/methanol to afford the corresponding ester (Structure 2). Structure 2 is treated with an organometallic agent, for example, an alkyl magnesium halide, to afford a compound of Structure 3. Structure 3 can be converted to a 2H-3,1-benzoxazine-2-one by treatment with a chloroformate, for example, ethyl chloroformate, followed by treatment with a base, for example potassium carbonate in DMF to afford a compound of Structure 4. Alternatively, Structure 4 can be obtained by treatment of Structure 3 with carbonyldiimidazole. Structure 4 can be halogenated at the 6-position by treatment with a brominating agent, for example, bromine, in an acid, for example trifluoroacetic acid, to afford a compound of Structure 5. Treatment of Structure 5 with an organometallic reagent, for example, an aryl boronic acid, in the presence of a transition metal catalyst, for example, [1,1'-bis(diphenylphosphino)ferrocene]dichloropalladium(II), in the presence of a base, for example, aqueous sodium carbonate, to afford a compound of Structure 6.

A compound of Structure 6 can be metallated to a compound of Structure 7 by treatment with a boronating agent, for example, 4,4,5,5-tetramethyl-1,3,2-dioxaborolane, in the presence of a transition metal catalyst, for example, [1,1'-bis(diphenylphosphino)ferrocene]dichloropalladium(II), in the presence of a base, for example, triethylamine, to afford a compound of Structure 6. Treatment of Structure 7 with an aryl halide, for example, an aryl bromide, in the presence of a transition metal catalyst, for example, [1,1'-bis(diphenylphosphino)ferrocene]dichloropalladium(II), in the presence of a base, for example, aqueous sodium carbonate, affords a compound of Structure 6. A compound of Structure 6 can be converted to the corresponding thione by treatment with a sulfurizing agent, for example, Lawesson's reagent, to afford a compound of Structure 8.

In certain embodiments, synthesis of 6-aryl- and 6-heteroaryl 1,4-dihydro-2H-3,1-benzoxazine-2-one (e.g. Structures 6, (+)-6 and (−)-6) and 6-aryl- and 6-heteroaryl 1,4-dihydro-2H-3,1-benzoxazine-2-thiones (Structures 8, (+)-8 and (−)-8)) is accomplished using Scheme II.

nyl magnesium bromide, affords a compound of Structure 3. Structure 3 can be converted to a 2H-3,1-benzoxazine-2-one by treatment with a chloroformate, for example, ethyl chloroformate, followed by treatment with a base, for example potassium carbonate in DMF to afford a compound of Structure 4. Alternatively, Structure 4 can be obtained by treatment of Structure 3 with carbonyldiimidazole. Structure 4 can be halogenated at the 6-position by treatment with a brominating agent, for example, bromine, in an acid, for example trifluoroacetic acid, to afford a compound of Structure 5. Treatment of Structure 5 with an organometallic reagent, for example, an aryl boronic acid, in the presence of a transition metal catalyst, for example, [1,1'-bis(diphenylphosphino)ferrocene] dichloropalladium(II), in the presence of a base, for example, aqueous sodium carbonate, affords a compound of Structure 6. A compound of Structure 6 can be converted to the corre-

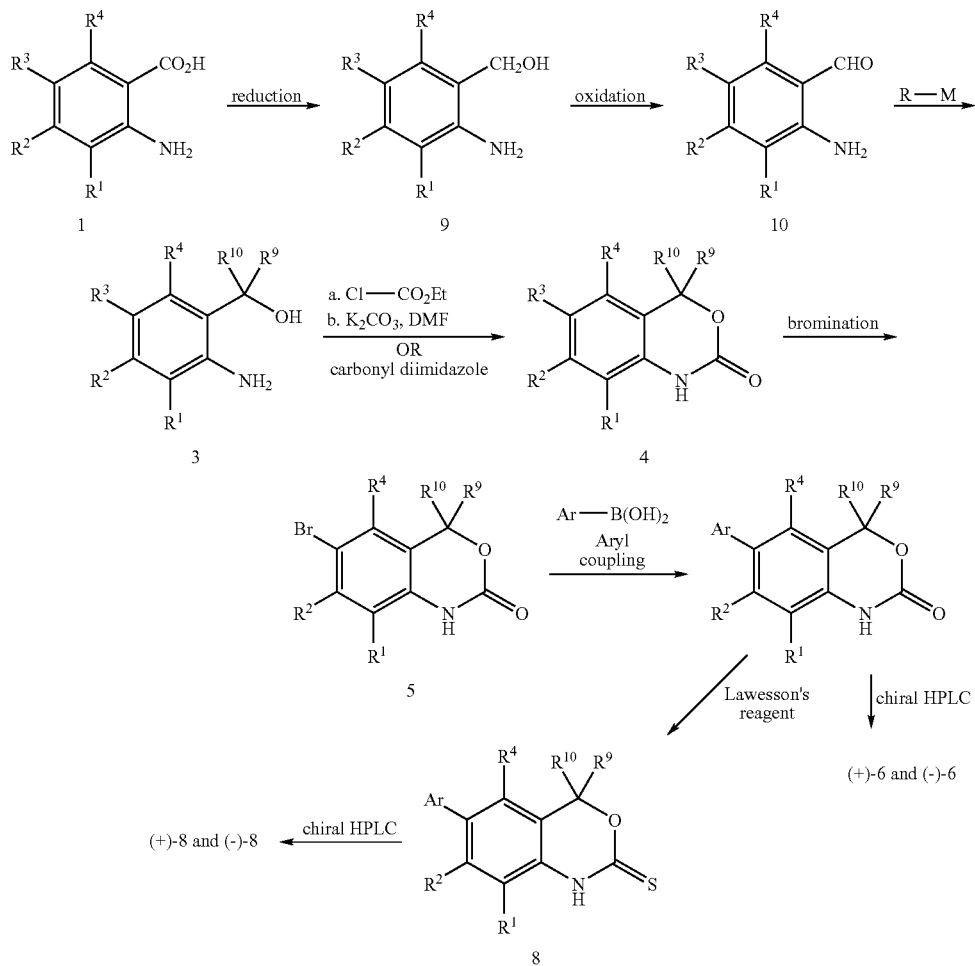

The process of Scheme II begins with the reduction of a 2-aminobenzoic acid derivative to the corresponding 2-aminobenzyl alcohol with a reducing agent, for example, lithium aluminum hydride to afford a compound of Structure 9. Treatment of 9 with an oxidant, for example, manganese dioxide, affords a compound of Structure 10. Treatment of 10 with an alkyl or aryl organometallic agent, for example, 4-fluorophesponding thione by treatment with a sulfurizing agent, for example, Lawesson's reagent, to afford a compound of Structure 8.

1,4-Dihydro-2H-3,1-benzoxazine-2-one compounds of Structure 6 (or any chiral synthetic precursor of Structure 6) can be separated into their corresponding enantiomers, (+)-6 and (−)-6 by chiral HPLC, with, for example, a preparative Chiracel OJ column eluted with hexanes:isopropanol. Alternatively, the enantiomers (+)-6 and (−)-6 could be prepared in enantiomerically enriched form via an enantiospecific synthesis of Structure 6, for example, by asymmetric carbonyl addition of Structure 10 to afford a compound of Structure 3 in enantiomerically enriched form.

1,4-Dihydro-2H-3,1-benzoxazine-2-thione compounds of Structure 8 (or any chiral synthetic precursor of Structure 8) can be separated into their corresponding enantiomers, (+)-8 and (−)-8 by chiral HPLC, with, for example, a preparative Chiracel OJ column eluted with hexanes:isopropanol. Alternatively, the enantiomers (+)-8 and (−)-8 could be prepared in enantiomerically enriched form via an enantiospecific synthesis of Structure 8, for example, by asymmetric carbonyl addition of Structure 10 to afford a compound of Structure 3 in enantiomerically enriched form.

An alternative synthesis of compounds of Structure 3 is depicted in Scheme III. A 2-aminobenzoic acid is treated with an amine, for example, methoxymethylamine, in the presence of an acylating agent, for example, DCC, to afford a compound of Structure 11. Treatment of 11 with an organometallic agent, for example, ethyl magnesium bromide, affords a compound of Structure 12. Treatment of 12 with an organometallic reagent, for example, methyl magnesium bromide, affords a compound of Structure 3.

Scheme III

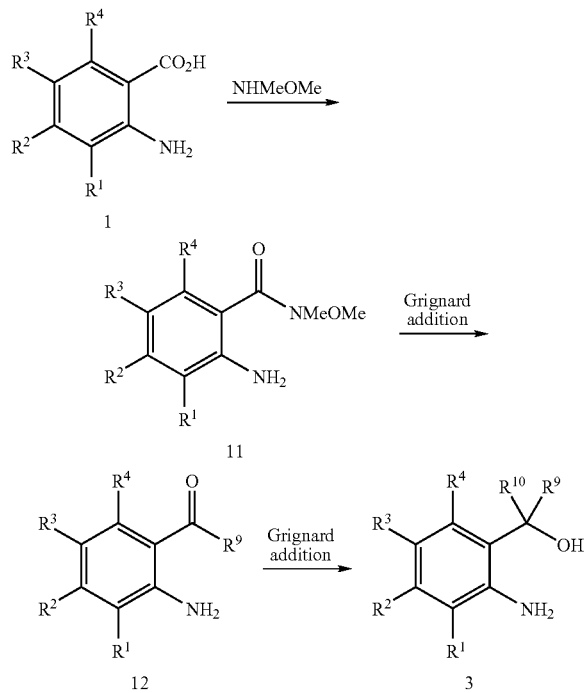

In certain embodiments, synthesis of 6-aryl- and 6-heteroaryl bromides, boronic acids, and boronate esters is accomplished using Schemes IV-VIII. The process of Scheme IV begins with the treatment of a phenol, for example 2-cyanophenol, with a brominating agent, for example N-bromosuccinimide, in the presence of a base, for example diisopropylamine, to afford an o-bromophenol (Structure 14). Structure 14 can be alkylated by treatment with an alkyl halide, for example, methyl iodide, in the presence of a base, for example potassium carbonate, to afford a compound of Structure 15. A compound of Structure 15 can be converted to a compound of Structure 16 by treatment with a boronating agent, for example, 4,4,5,5-tetramethyl-1,3,2-dioxaborolane, in the presence of a transition metal catalyst, for example, $Pd_2dba_3$, and a phosphorus ligand, for example, 2-(dicyclohexylphosphino)biphenyl, in the presence of a base, for example, triethylamine, to afford a compound of Structure 16.

Scheme IV

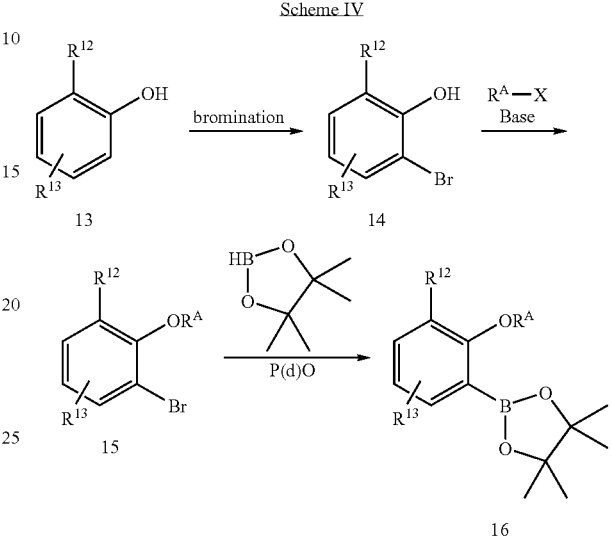

$R^A$ = alkyl, arylmethyl, trialkylsilyl, alkylarylsilyl.

The process of Scheme V begins with a metallation of a 1,3-dimethoxybenzene of Structure 17, for example, 2,4-dimethoxybenzonitrile, with a base, for example lithium tetramethylpiperidine, and a silylating agent, for example, chlorotrimethylsilane, to afford a compound of Structure 18. Compound 18 is converted to the corresponding bromide by treatment with a brominating agent, for example, N-bromosuccinimide, to afford a compound of Structure 19.

Scheme V

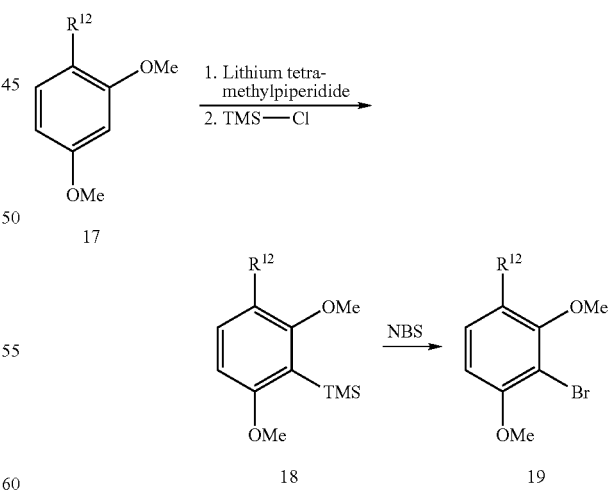

The process of Scheme VI is the treatment of Structure 20, for example, 1-indanone, with bromine in the presence of a Lewis Acid, for example, aluminum chloride, to afford a compound of Structure 21.

Scheme VI

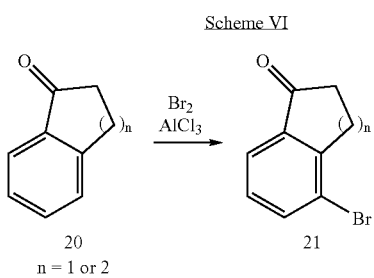

n = 1 or 2

The process of Scheme VII is the treatment of a 2-nitrohalobenzene (Structure 22), for example, 1-bromo-2-nitrobenzene, with a vinyl Grignard reagent, for example vinylmagnesium bromide, to afford a compound of Structure 23.

Scheme VII

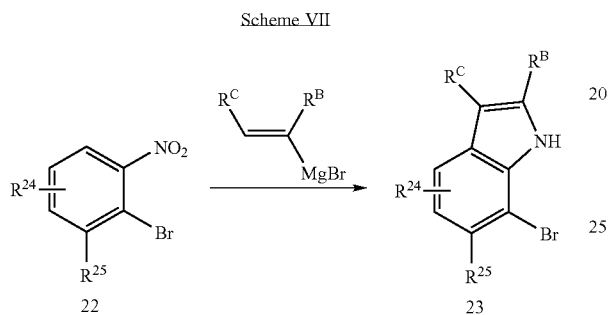

$R^B$ and $R^C$ are independently H, alkyl, aryl, heteroaryl.

The process of Scheme VIII is the treatment of Structure 24 with an acid, for example, hydrochloric acid in acetic acid, to afford a compound of Structure 25.

Scheme VIII

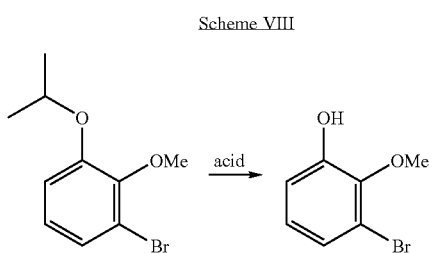

The synthesis of compounds of Structure 27 and 28 is depicted in Scheme IX and begins with the treatment of Structure 26 with a reducing agent, for example zinc dust, to afford the corresponding amino compound of Structure 27. Structure 27 can be alkylated, acylated, or sulfonylated be treatment, for example, with methyl iodide, methyl chloroformate, or methanesulfonyl chloride, respectively, to afford compounds of Structure 28.

Scheme IX

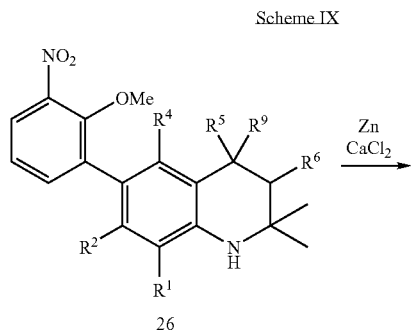

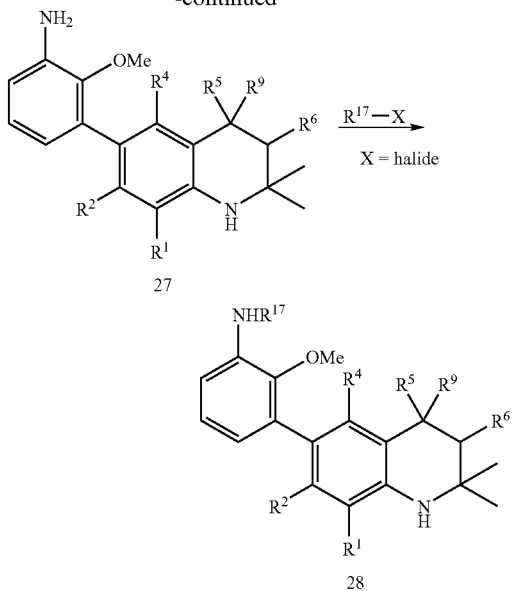

The synthesis of compounds of Structure 31 and 32 is depicted in Scheme X. Deprotection of an ether of Structure 29 can be accomplished by treatment with an acid, for example methanesulfonic acid to afford a phenol of Structure 30. Treatment of Structure 30 with a haloformate or haloacetate, for example, ethyl bromoacetate, followed by reduction with, for example zinc dust, affords a compound of Structure 31. Treatment of Structure 31 with an alkylating agent, for example, methyl iodide, in the presence of a base, for example, sodium hydride, affords a compound of Structure 32. Alternatively, treatment of Structure 30 with a reducing agent, for example, zinc dust, affords a compound of Structure 30A. Alternatively, treatment of Structure 30 with an alkylating agent, for example, allyl bromide, in the presence of a base, for example potassium carbonate, affords a compound of Structure 30B.

Scheme X

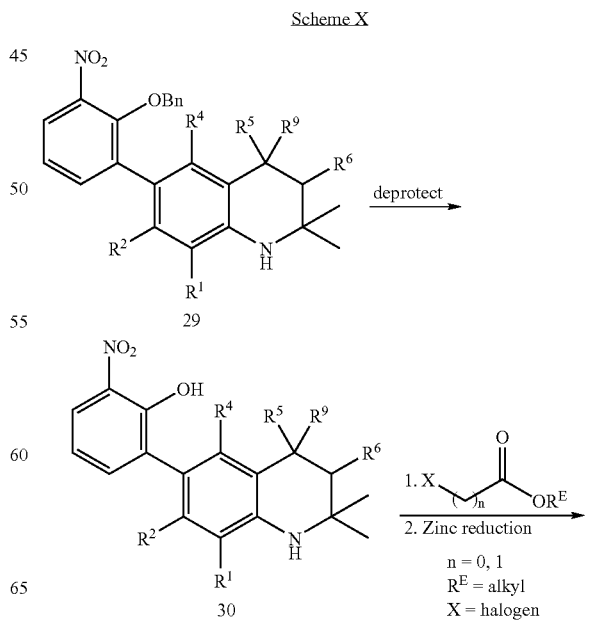

-continued
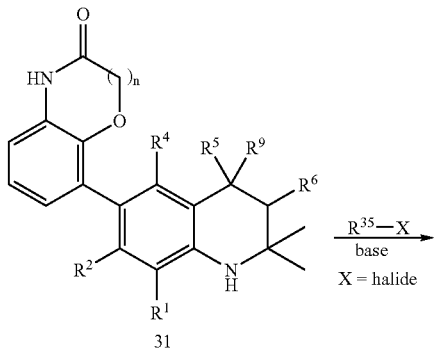
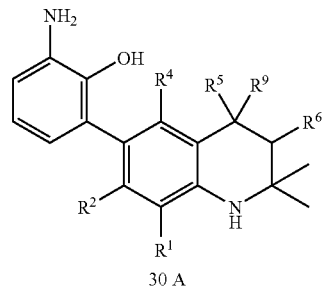
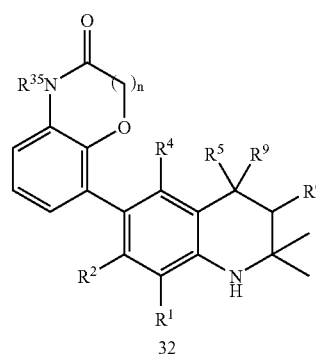
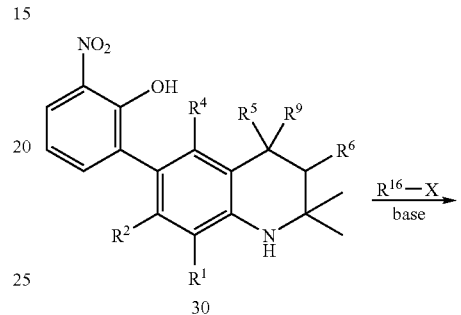
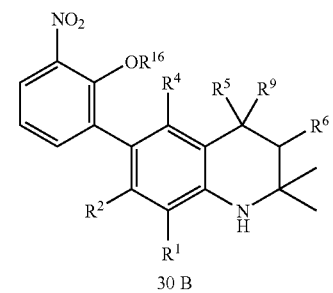
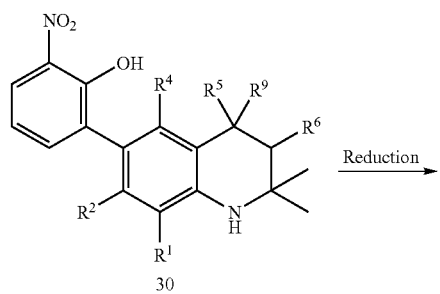
The synthesis of compounds of Structure 34 is depicted in Scheme XI. A nitro derivative of Structure 33 is treated with an ethenyl magnesium halide, for example, vinyl magnesium bromide, to afford a compound of Structure 34. Treatment of Structure 33 with a reducing agent, for example, zinc metal, affords a compound of Structure 34B.
Scheme XI
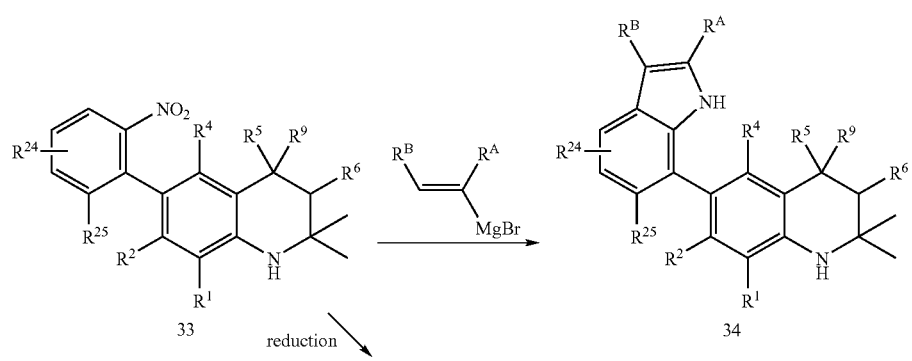

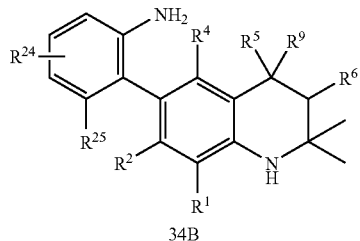

34B

The synthesis of compounds of Structure 36 and 37 is depicted in Scheme XII. An indole compound of Structure 35 can be alkylated at the 3-position of the indole by treatment with an ethenyl ketone, for example, methyl vinyl ketone, in the presence of a Lewis acid, for example, indium trichloride, to afford a compound of Structure 36.

compound of Structure 37 can be treated with a reducing agent, for example, sodium cyanoborohydride, in the presence of an acid, for example, acetic acid, to afford a compound of Structure 41.

Scheme XII

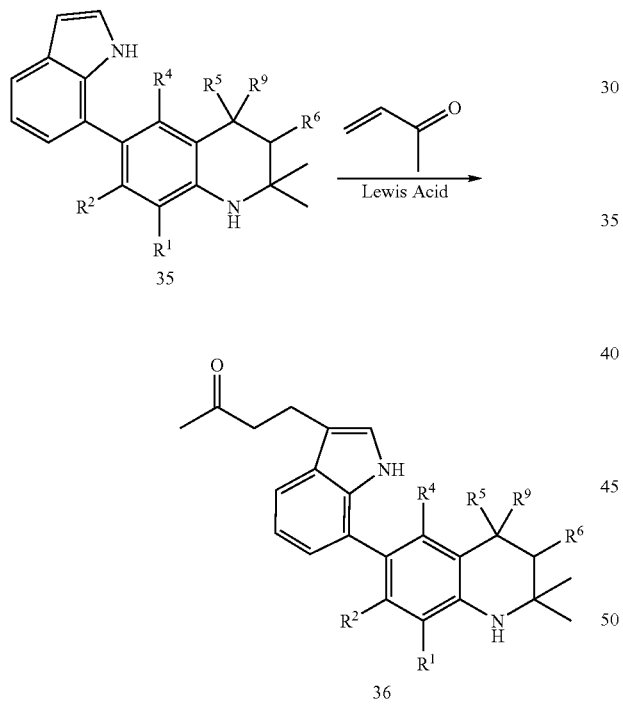

Scheme XIII

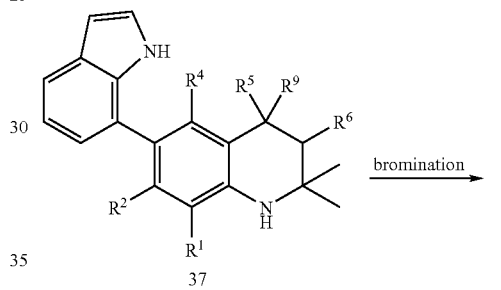

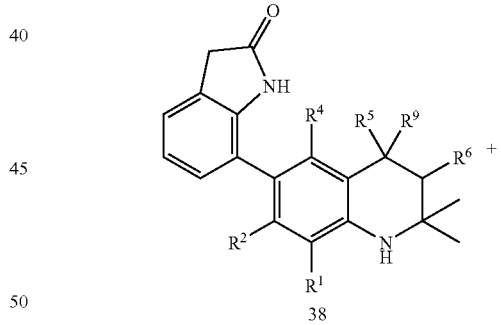

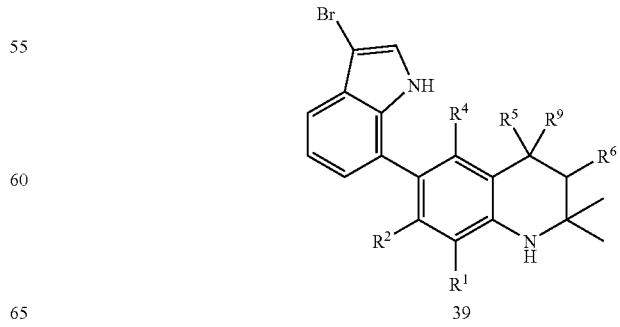

The synthesis of compounds of Structure 38, 39 and 40 is depicted in Scheme XIII. An indole of Structure 37 is treated with a brominating agent, for example, N-bromosuccinimide, in the presence of water, to afford a mixture of compounds of Structure 38 and 39. Structure 39 may be treated with an organometallic reagent, for example, an aryl boronic acid, in the presence of a transition metal catalyst, for example, [1,1'-bis(diphenylphosphino)ferrocene]dichloropalladium(II), in the presence of a base, for example, aqueous sodium carbonate, to afford a compound of Structure 40. Alternatively, a -continued

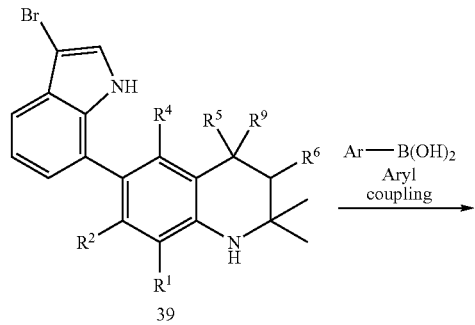

39

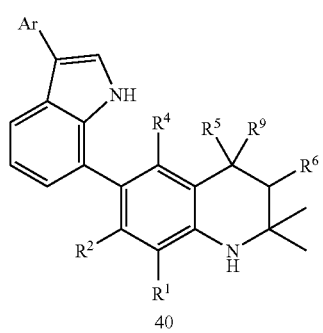

40

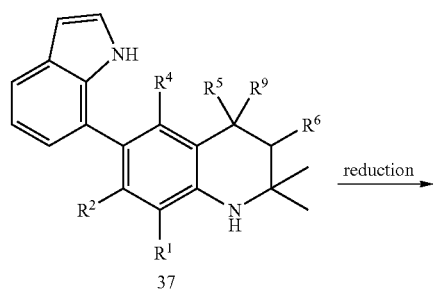

37

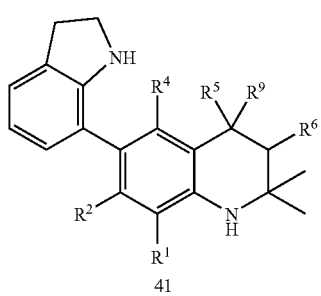

41

The synthesis of compounds of Structure 43 is depicted in Scheme XIV. A compound of Structure 42 is treated with hydroxylamine hydrochloride or an alkoxy amine hydrochloride to afford a compound of Structure 43.

Scheme XIV

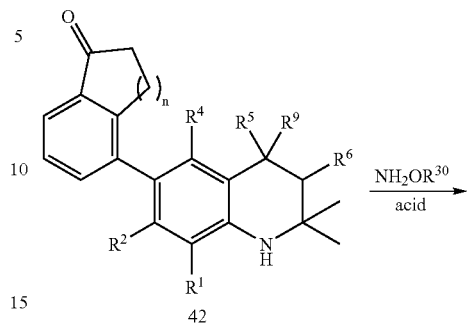

42

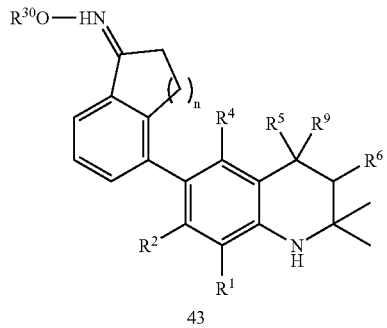

43

In certain embodiments, the invention provides a salt corresponding to any of the compounds provided herein. In certain embodiments, the invention provides a salt corresponding to a selective mineralocorticoid receptor modulator. In certain embodiments, the invention provides a salt corresponding to a selective mineralocorticoid receptor binding agent. In certain embodiments, a salt is obtained by reacting a compound with an inorganic acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

In certain embodiments, one or more carbon atoms of a compound of the present invention is replaced with silicon. See e.g. WO 03/037905A1; Tacke and Zilch, Endeavour, New Series, 10, 191-197 (1986); Bains and Tacke, Curr. Opin. Drug Discov Devel. July:6(4):526-43(2003). In certain embodiments, compounds of the present invention comprising one or more silicon atoms possess certain desired properties, including, but not limited to, greater stability and/or longer half-life in a patient, when compared to the same compound in which none of the carbon atoms have been replaced with a silicon atom.

Certain Assays

In certain embodiments, compounds of the present invention are capable of modulating activity of mineralocorticoid receptors in a "co-transfection" assay (also called a "cis-trans" assay), which has been discussed previously. See e.g. Evans et al., Science, 240:889-95 (1988); U.S. Pat. Nos. 4,981,784 and 5,071,773; Pathirana et al., "Nonsteroidal Human Progesterone Receptor Modulators from the Marie Alga Cymopolia Barbata," Mol. Pharm. 47:630-35 (1995)).

Modulating activity in a co-transfection assay has been shown to correlate with in vivo modulating activity. Thus, in certain embodiments, such assays are predictive of in vivo activity. See, e.g. Berger et al., *J. Steroid Biochem. Molec. Biol.* 41:773 (1992).

In certain co-transfection assays, two different co-transfection plasmids are prepared. In the first co-transfection plasmid, cloned cDNA encoding an intracellular receptor (e.g., mineralocorticoid receptor) is operatively linked to a constitutive promoter (e.g., the SV 40 promoter). In the second co-transfection plasmid, cDNA encoding a reporter protein, such as firefly luciferase (LUC), is operatively linked to a promoter that is activated by a receptor-dependant activation factor. Both co-transfection plasmids are co-transfected into the same cells. Expression of the first co-transfection plasmid results in production of the intracellular receptor protein. Activation of that intracellular receptor protein (e.g. by binding of an agonist) results in production of a receptor-dependant activation factor for the promoter of the second co-transfection plasmid. That receptor-dependant activation factor in turn results in expression of the reporter protein encoded on the second co-transfection plasmid. Thus, reporter protein expression is linked to activation of the receptor. Typically, that reporter activity can be conveniently measured (e.g. as increased luciferase production).

Certain co-transfection assays can be used to identify agonists, partial agonists, and/or antagonists of intracellular receptors. In certain embodiments, to identify agonists, co-transfected cells are exposed to a test compound. If the test compound is an agonist or partial agonist, reporter activity is expected to be higher compared to co-transfected cells in the absence of the test compound. In certain embodiments, to identify antagonists, the cells are exposed to a known agonist (e.g., the natural ligand for the receptor) in the presence and absence of a test compound. If the test compound is an antagonist, reporter activity is expected to be lower than that of cells exposed only to the known agonist.

In certain embodiments, compounds of the invention are used to detect the presence, quantity and/or state of receptors in a sample. In certain of such embodiments, samples are obtained from a patient. In certain embodiments, compounds are radio—or isotopically—labeled. For example, compounds of the present invention that selectively bind mineralocorticoid receptors may be used to determine the presence or amount of such receptors in a sample, such as cell homogenates and lysates.

Certain Pharmaceutical Agents

In certain embodiments, at least one selective mineralocorticoid receptor modulator, or pharmaceutically acceptable salt, ester, amide, and/or prodrug thereof, either alone or combined with one or more pharmaceutically acceptable carriers, forms a pharmaceutical agent. Techniques for formulation and administration of compounds of the present invention may be found for example, in "Remington's Pharmaceutical Sciences," Mack Publishing Co., Easton, Pa., 18th edition, 1990.

In certain embodiments, a pharmaceutical agent comprising one or more compounds of the present invention is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present invention is a liquid (e.g. a suspension, elixir and/or solution). In certain of such embodiments, a liquid pharmaceutical agent comprising one or more compounds of the present invention is prepared using ingredients known in the art, including, but not limited to, water, glycols, oils, alcohols, flavoring agents, preservatives, and coloring agents.

In certain embodiments, a pharmaceutical agent comprising one or more compounds of the present invention is a solid (e.g. a powder, tablet, and/or capsule). In certain of such embodiments, a solid pharmaceutical agent comprising one or more compounds of the present invention is prepared using ingredients known in the art, including, but not limited to, starches, sugars, diluents, granulating agents, lubricants, binders, and disintegrating agents.

In certain embodiments, a pharmaceutical agent comprising one or more compounds of the present invention is formulated as a depot preparation. Certain of such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present invention comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present invention comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g. polyvinyl pyrrolidone; and other sugars or polysaccharides may substitute for dextrose.

In certain embodiments, a pharmaceutical agent comprising one or more compounds of the present invention comprises a sustained-release system. A non-limiting example of such a sustained-release system is a semi-permeable matrix of solid hydrophobic polymers. In certain embodiments, sustained-release systems may, depending on their chemical nature, release compounds over a period of hours, days, weeks or months.

Certain compounds used in pharmaceutical agent of the present invention may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical agent comprising one or more compounds of the present invention comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present invention is formulated as a prodrug. In certain embodiments, prodrugs are useful because they are easier to administer than the corresponding active form. For example, in certain instances, a prodrug may be more bioavailable (e.g. through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical agent comprising one or more compounds of the present invention is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present invention is administered in the form of a dosage unit (e.g. tablet, capsule, bolus, etc.). In certain embodiments, such dosage units comprise a selective a mineralocorticoid receptor modulator in a dose from about 1 µg/kg of body weight to about 50 mg/kg of body weight. In certain embodiments, such dosage units comprise a selective a mineralocorticoid receptor modulator in a dose from about 2 µg/kg of body weight to about 25 mg/kg of body weight. In certain embodiments, such dosage units comprise a selective a mineralocorticoid receptor modulator in a dose from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present invention is prepared for oral administration. In certain of such embodiments, a pharmaceutical agent is formulated by combining one or more compounds of the present invention with one or more pharmaceutically acceptable carriers. Certain of such carriers enable compounds of the invention to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present invention and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present invention in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present invention are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g. in ampoules or in multi-dose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g. dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the invention and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for a pharmaceutical agent of the present invention can be chosen in view of a particular patient's condition. (See e.g. Fingl et al. 1975, in "The Pharmacological Basis of Therapeutics", Ch. 1 p. 1). In certain embodiments, a pharmaceutical agent is administered as a single dose. In certain embodiments, a pharmaceutical agent is administered as a series of two or more doses administered over one or more days.

In certain embodiments, a pharmaceutical agent of the present invention is administered to a patient between about 0.1% and 500%, more preferably between about 25% and 75% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg of a compound of the present invention. In certain embodiments, a daily dosage regimen is administered as a single daily dose. In certain embodiments, a daily dosage regimen is administered as two, three, four, or more than four doses.

In certain embodiments, a pharmaceutical agent of the present invention is administered by continuous intravenous infusion. In certain of such embodiments, from 0.1 mg to 500 mg of a composition of the present invention is administered per day.

In certain embodiments, a pharmaceutical agent of the invention is administered for a period of continuous therapy. For example, a pharmaceutical agent of the present invention may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present invention at an amount sufficient to achieve a desired effect. In certain of such embodiments the plasma concentration is maintained above the minimal effective concentration (MEC). In certain embodiments, pharmaceutical agents of the present invention are administered with a dosage regimen designed to maintain a concentration above the MEC for 10-90% of the time, between 30-90% of the time, or between 50-90% of the time.

In certain embodiments in which a pharmaceutical agent is administered locally, the dosage regimen is adjusted to achieve a desired local concentration of a compound of the present invention.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Certain Combination Therapies

In certain embodiments, one or more pharmaceutical agents of the present invention are co-administered with one or more other pharmaceutical agents. In certain embodiments, such one or more other pharmaceutical agents are designed to treat the same disease or condition as the one or more pharmaceutical agents of the present invention. In certain embodiments, such one or more other pharmaceutical agents are designed to treat a different disease or condition as the one or more pharmaceutical agents of the present invention. In certain embodiments, such one or more other pharmaceutical agents are designed to treat an undesired effect of one or more pharmaceutical agents of the present invention.

In certain embodiments, one or more pharmaceutical agents of the present invention is co-administered with another pharmaceutical agent to treat an undesired effect of that other pharmaceutical agent. In certain embodiments, one or more pharmaceutical agents of the present invention and one or more other pharmaceutical agents are administered at the same time. In certain embodiments, one or more pharmaceutical agents of the present invention and one or more other pharmaceutical agents are administered at the different times. In certain embodiments, one or more pharmaceutical agents of the present invention and one or more other pharmaceutical agents are prepared together in a single formulation. In certain embodiments, one or more pharmaceutical agents of the present invention and one or more other pharmaceutical agents are prepared separately.

Examples of pharmaceutical agents that may be co-administered with a pharmaceutical agent of the present invention include, but are not limited to, analgesics (e.g., acetaminophen); anti-inflammatory agents, including, but not limited to non-steroidal anti-inflammatory drugs (e.g. ibuprofen, COX-1 inhibitors, and COX-2, inhibitors); salicylates; antibiotics; antivirals; antifungal agents; antidiabetic agents (e.g. biguanides, glucosidase inhibitors, insulins, sulfonylureas, and thiazolidenediones); adrenergic modifiers; diuretics; hormones (e.g. anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Certain Indications

In certain embodiments, the invention provides methods of treating a patient comprising administering one or more compounds of the present invention. In certain embodiments, such patient suffers from a mineralocorticoid receptor mediated condition. In certain embodiments, a patient is treated prophylactically to reduce or prevent the occurrence of a condition.

In certain embodiments, one or more compounds of the present invention is used to treat one or more conditions selected from the group consisting of congestive heart failure, hypertension, fibrosis (including, but not limited to, cardiac, kidney, and lung), primary hyperaldosteronism, hypokalemia, and liver cirrhosis. In certain such embodiments, the patient suffers from a condition including, but not limited to, hypoaldosteronism, hyperkalemia, metabolic acidosis, hypoadrenocorticoidism, and Addison's disease.

EXAMPLES

The following examples, including experiments and results achieved, are provided for illustrative purposes only and are not to be construed as limiting the present invention.

Example 1

General Method 1: Addition of an alkyl or aryl magnesium halide to ester or aldehyde. A solution of an alkyl or an aryl magnesium halide (solution in ether, 4-5 equiv) is added to a solution of an ester or aldehyde (1 equiv) in ether (0.5 M) at 0° C. The reaction is stirred for 1-2 hours, quenched slowly with water, and extracted with ethyl acetate. The organic layer from that extraction is washed with brine, dried over magnesium sulfate, filtered, and concentrated under reduced pressure. Flash chromatography (hexanes:ethyl acetate) affords the desired compound.

General Method 2: Preparation of a 1,4-dihydro-2H-3,1-benzoxazin-2-one. Methyl chloroformate (1.2 equiv) is added to a solution of a 2-(aminophenyl)alkanol (1 equiv) and DMAP (0.10 equiv) in pyridine (1 M) at 0° C. Additional pyridine is added as needed to keep the precipitates from accumulating. The solution is allowed to warm to room temperature and stirred for 2 hours. Sodium bisulfate (2N) and ethyl acetate are added, resulting in an aqueous layer and a first organic layer. The first organic layer is collected and the aqueous layer extracted with ethyl acetate. The organic layer from that extraction is combined with the first organic layer and that combined organic layer is washed sequentially with water and brine, dried over magnesium sulfate, filtered, and concentrated under reduced pressure to afford a solid. To the solid is added potassium carbonate (2 equiv) in DMF (0.5-0.7 M) and that mixture is heated to 100° C. for 1-4 hours. The mixture is cooled and poured into ethyl acetate:water, resulting in a first organic layer and an aqueous layer. The first organic layer is collected and the aqueous layer is extracted with ethyl acetate. The organic layer from that extraction is combined with the collected first organic layer, and the combined organic layers are washed sequentially with water and brine, dried over magnesium sulfate, filtered, and concentrated to afford the 1,4-dihydro-2H-3,1-benzoxazin-2-one.

General Method 3: Bromination of a 1,4-dihydro-2H-3,1-benzoxazin-2-one to a 6-bromo-1,4-dihydro-2H-3,1-benzoxazin-2-one. To a suspension of 1,4-dihydro-2H-3,1-benzoxazin-2-one (1 equiv) in 4:1 acetic acid:trifluoroacetic acid (0.4 M) is added bromine (1.1 equiv) dropwise and the mixture is stirred at room temperature overnight. Ethyl acetate and sodium thiosulfate are added, resulting in an aqueous layer and an organic layer. The organic layer is washed with aqueous sodium bicarbonate, brine, dried over magnesium sulfate, filtered, and concentrated under reduced pressure to afford a 6-bromo-1,4-dihydro-2H-3,1-benzoxazin-2-one.

General method 4: Palladium-catalyzed Suzuki cross-coupling of an aryl halide and an aryl boronic acid or aryl pinacol boronate. In a Schlenck reaction flask, a mixture of an aryl bromide (1 equiv); an aryl boronic acid or aryl pinacol boronate (1.0-1.3 equiv); and [1,1'-bis(diphenylphosphino)ferrocene]dichloropalladium(II) complex with dichloromethane (3-10 mol %) is placed under vacuum, and backfilled with nitrogen. Dioxane (0.1-0.2 M) and 2M sodium carbonate (2 equiv) are introduced sequentially. The mixture is heated (95-100° C.) for 16-24 h. The mixture is partitioned between saturated ammonium chloride and EtOAc, resulting in a first organic layer and an aqueous layer. The first organic layer is collected and the aqueous layer is extracted with EtOAc. The organic layer from that extraction is combined with the first collected organic layer and that combined organic layer is washed with brine, dried over magnesium sulfate, filtered, and concentrated under reduced pressure. Flash chromatography (silica gel, EtOAc/hexanes or other specified solvent), preparative thin-layer chromatography (prep TLC, EtOAc/hexanes or other specified solvents), preparative HPLC and/or recrystallization affords the desired compound.

Methyl 2-amino-6-chlorobenzoate (Structure 2 of Scheme I)

To prepare this compound, trimethylsilyldiazomethane (2 M in hexanes, 1.5 equiv) was added to a solution of the 2-amino-6-chlorobenzoic acid (1 equiv) in 2:1 benzene:methanol (0.2-0.3 M) at room temperature. After 1 hour, the solvent was removed under reduced pressure to afford methyl 2-amino-6-chlorobenzoate in 96% yield. That product was used without further purification or was purified by flash chromatography (7:3 hexanes:ethyl acetate) in 91% yield.

2-(2-Amino-6-chlorophenyl)propan-2-ol (Structure 3 of Scheme I)

This compound was prepared using General Method 1 (EXAMPLE 1) from methyl 2-amino-6-chlorobenzoate (1.7 g, 9.2 mmol) and methyl magnesium bromide (3 M in diethyl ether, 12.2 mL) in 45 mL ether to afford 1.5 g (89%) of 2-(2-amino-6-chlorophenyl)propan-2-ol after flash chromatography (5:3 hexanes:ethyl acetate).

5-Chloro-1,4-dihydro-4,4-dimethyl-2H-3,1-benzoxazin-2-one (Structure 4 of Scheme I)

This compound was prepared using General Method 2 (EXAMPLE 1) from 2-(2-amino-6-chlorophenyl)propan-2-ol (1.33 g, 7.2 mmol) to afford 1.28 g (85%) of 5-chloro-1,4-dihydro-4,4-dimethyl-2H-3,1-benzoxazin-2-one, an off-white solid.

6-Bromo-5-chloro-1,4-dihydro-4,4-dimethyl-2H-3,1-benzoxazin-2-one (Structure 5 of Scheme I)

This compound was prepared using General Method 3 (EXAMPLE 1) from 5-chloro-1,4-dihydro-4,4-dimethyl-2H-3,1-benzoxazin-2-one (40 mg) to afford 47 mg (85%) of 6-bromo-5-chloro-1,4-dihydro-4,4-dimethyl-2H-3,1-benzoxazin-2-one, a white solid, after flash chromatography (2:1 hexanes:ethyl acetate).

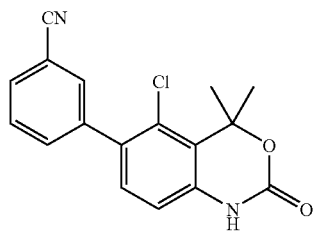

5-Chloro-6-(3-cyanophenyl)-1,4-dihydro-4,4-dimethyl-2H-3,1-benzoxazin-2-one (Compound 101, Structure 6 of Scheme I)

Compound 101 was prepared using General Method 4 (EXAMPLE 1) from 6-bromo-5-chloro-1,4-dihydro-4,4-dimethyl-2H-3,1-benzoxazin-2-one (15 mg, 0.052 mmol) and 3-cyanophenylboronic acid (12 mg, 0.083 mmol) to afford 13 mg (81%) of Compound 101 after flash chromatography (3:2 hexanes:Ethyl acetate). $^1$H NMR (400 MHz, CDCl$_3$) δ 9.45 (broad s, 1H), 7.65 (d, J=6.9, 1H), 7.64 (d, J=1.1, 1H), 7.57 (dd, J=1.3, 7.9, 1H), 7.52 (t, J=7.6, 1H), 7.14 (d, J=8.0, 1H), 6.87 (d, J=8.1, 1H), 1.95 (s, 6H).

Example 2

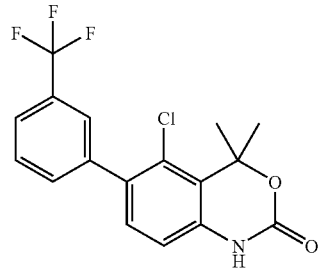

5-Chloro-1,4-dihydro-4,4-dimethyl-6-[3-(trifluoromethyl)phenyl]-2H-3,1-benzoxazin-2-one (Compound 102, Structure 6 of Scheme I)

Compound 102 was prepared using General Method 4 (EXAMPLE 1) from 6-bromo-5-chloro-1,4-dihydro-4,4-dimethyl-2H-3,1-benzoxazin-2-one (25 mg, 0.086 mmol) and 3-(trifluoromethyl)phenylboronic acid (20 mg, 0.10 mmol) to afford 28 mg (92%) of Compound 102 after flash chromatography (2:1 hexanes:Ethyl acetate). $^1$H NMR (400 MHz, CDCl$_3$) δ 9.71 (broad s, 1H), 7.61 (m, 1H), 7.53 (s, 1H), 7.52 (d, J=4.2, 2H), 7.17 (d, J=8.1, 1H), 6.88 (d, J=8.2, 1H), 1.96 (s, 6H).

Example 3

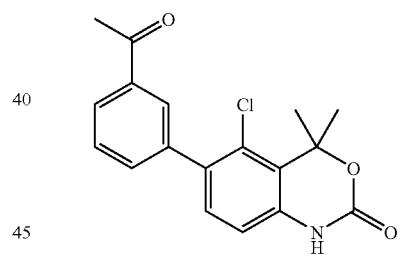

6-(3-Acetylphenyl)-5-chloro-1,4-dihydro-4,4-dimethyl-2H-3,1-benzoxazin-2-one (Compound 103, Structure 6 of Scheme I)

Compound 103 was prepared using General Method 4 (EXAMPLE 1) from 6-bromo-5-chloro-1,4-dihydro-4,4-dimethyl-2H-3,1-benzoxazin-2-one (25 mg, 0.086 mmol) and 3-acetylphenylboronic acid (16 mg, 0.10 mmol) to afford 27 mg (95%) of Compound 103. $^1$H NMR (400 MHz, CDCl$_3$) δ 9.65 (broad s, 1H), 7.95 (m, 1H), 7.92 (s, 1H), 7.54 (m, 1H), 7.52 (m, 1H), 7.18 (d, J=8.1, 1H), 6.88 (d, J=8.3, 1H), 2.62 (s, 3H), 1.95 (s, 6H).

Example 4

General Method 5: Conversion of a 1,4-dihydro-2H-3,1-benzoxazin-2-one to a 1,4-dihydro-2H-3,1-benzoxazin-2-thione. A solution of a 1,4-dihydro-2H-3,1-benzoxazin-2-one (1 equiv) and [2,4-bis(4-methoxyphenyl)-1,3-dithia-2,4-diphosphetane-2,4-disulfide (Lawesson's reagent, 1.5 equiv) is combined in refluxing xylenes (0.05-0.1 M) for 6-24 hours. The solvent is removed under reduced pressure and the resultant solid is purified by flash chromatography.

δ 9.89 (broad s, 1H), 7.34 (m, 3H), 7.25 (m, 1H), 7.17 (dd, J=3.4, 8.0, 1H), 6.89 (dd, J=3.4, 8.3, 1H), 1.97 (s, 6H).

Example 6

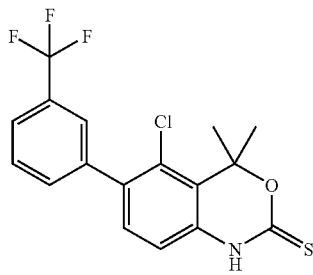

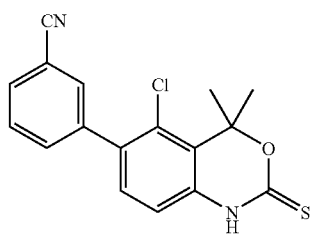

5-Chloro-1,4-dihydro-4,4-dimethyl-6-[3-(trifluoromethyl)phenyl]-2H-3,1-benzoxazin-2-thione (Compound 104, Structure 8 of Scheme I)

5-Chloro-6-(3-cyanophenyl)-1,4-dihydro-4,4-dimethyl-2H-3,1-benzoxazin-2-thione (Compound 106, Structure 8 of Scheme I)

Compound 104 was prepared using General Method 5 (EXAMPLE 4) from Compound 103 (EXAMPLE 3) (10 mg, 0.028 mmol) to afford 9 mg (86%) of Compound 104 after flash chromatography (4:1 hexanes:ethyl acetate). $^1$H NMR (400 MHz, CDCl$_3$) δ 9.48 (broad s, 1H), 7.64 (d, J=7.12, 1H), 7.59 (s, 1H), 7.54 (m, 2H), 7.22 (d, J=8.3, 1H), 6.83 (d, J=8.3, 1H), 1.98 (s, 6H).

Compound 106 was prepared using General Method 5 (EXAMPLE 4) from Compound 101 (7 mg, 0.022 mmol) to afford 3.1 mg (43%) of Compound 106 after flash chromatography (4:1 hexanes:ethyl acetate). $^1$H NMR (400 MHz, CDCl$_3$) δ 9.22 (broad s, 1H), 7.67 (d, J=7.3, 1H), 7.56 (m, 1H), 7.54 (m, 2H), 7.19 (d, J=8.1, 1H), 6.80 (d, J=8.1, 1H), 1.98 (s, 6H).

Example 5

Example 7

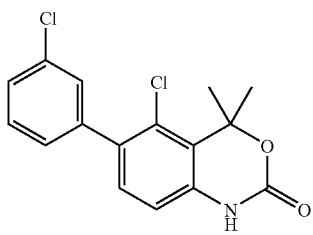

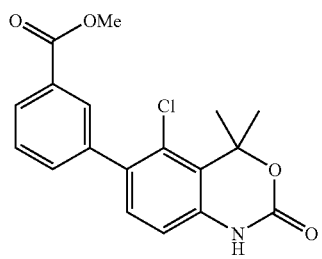

5-Chloro-6-(3-chlorophenyl)-1,4-dihydro-4,4-dimethyl-2H-3,1-benzoxazin-2-one (Compound 105, Structure 6 of Scheme I)

6-(3-Carboxymethylphenyl)-5-chloro-1,4-dihydro-4,4-dimethyl-2H-3,1-benzoxazin-2-one (Compound 107, Structure 6 of Scheme I)

Compound 105 was prepared using General Method 4 (EXAMPLE 1) from 6-bromo-5-chloro-1,4-dihydro-4,4-dimethyl-2H-3,1-benzoxazin-2-one (25 mg, 0.086 mmol) and 3-chlorophenylboronic acid (16 mg, 0.10 mmol) to afford 22 mg (79%) of Compound 105. $^1$H NMR (400 MHz, CDCl$_3$)

Compound 107 was prepared using General Method 4 (EXAMPLE 1) from 6-bromo-5-chloro-1,4-dihydro-4,4-dimethyl-2H-3,1-benzoxazin-2-one (83 mg, 0.29 mmol) and 3-carboxymethylphenylboronic acid (67 mg, 0.37 mmol) to afford Compound 107. $^1$H NMR (500 MHz, CDCl$_3$) δ 9.34 (s, 1H), 8.06 (d, J=7.6, 1H), 8.04 (t, dd, J=1.8, 1.5, 1H), 7.53-7.60 (m, 1H), 7.51 (dd, J=7.6, 7.6, 1H), 7.20 (d, J=8.2, 1H), 6.87 (d, J=8.2, 1H), 3.94 (s, 3H), 1.98 (s, 6H).

Example 8

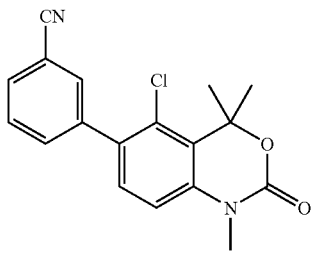

5-Chloro-6-(3-cyanophenyl)-1,4-dihydro-1,44-trimethyl-2H-3,1-benzoxazin-2-one (Compound 108)

To prepare compound 108, iodomethane (20 mg, 0.14 mmol) was added to a mixture of Compound 101 (EXAMPLE 1) (13 mg, 0.049 mmol) and sodium hydride (60% in mineral oil, 6 mg, 0.14 mmol) in 1 mL THF. After 1.5 hour, the mixture was quenched with saturated ammonium chloride, and the mixture was extracted with ether. The organic layer from that extraction was washed with water, dried over magnesium sulfate, filtered, and concentrated under reduced pressure. Flash chromatography (2:1 hexanes:ethyl acetate) afforded 11 mg (69%) of Compound 108. $^1$H NMR (500 MHz, CDCl$_3$) δ 7.67-7.70 (m, 1H), 7.64-7.67 (m, 1H), 7.59-7.63 (m, 1H), 7.55 (dd, J=7.6, 7.6, 1H), 7.25 (d, J=8.2, 1H), 6.95 (d, J=8.2, 1H), 3.44 (s, 3H), 1.92 (s, 6H).

Example 9

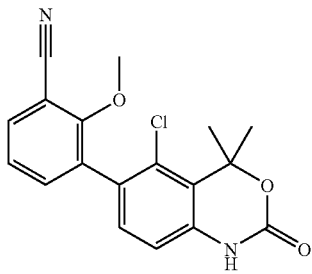

5-Chloro-6-(3-cyano-2-methoxyphenyl)-1,4-dihydro-4,4-dimethyl-2H-3,1-benzoxazin-2-one (Compound 109, Structure 6 of Scheme I)

To prepare compound 109, first 2-Methoxy-3-(4,4,5,5-tetramethyl-1,3,2-dioxaborolan-2-yl)benzonitrile was prepared by combining 3-bromo-2-cyanobenzonitrile (1.0 g), P(cyclohexyl)$_2$biphenyl (200 mg), Pd$_2$dba$_3$ (132 mg) and flushing with nitrogen. Then dioxane (32 mL), triethylamine (2.7 mL) and pinacolborane (1.5 mL) was added and the mixture heated at reflux. After 16 h, the reaction was quenched with saturated ammonium chloride, and extracted with EtOAc. The organic layers were washed with brine, dried over magnesium sulfate, an filtered. Flash chromatography (80% dichloromethane/hexanes) affords 2-methoxy-3-(4,4,5,5-tetramethyl-1,3,2-dioxaborolan-2-yl)benzonitrile (416 mg).

Compound 109 was prepared using General Method 4 (EXAMPLE 1) from 6-bromo-5-chloro-1,4-dihydro-4,4-dimethyl-2H-3,1-benzoxazin-2-one (29 mg, 0.10 mmol) and 2-methoxy-3-(4,4,5,5-tetramethyl-1,3,2-dioxaborolan-2-yl)benzonitrile (31 mg, 0.12 mmol) to afford 7 mg (21%) of Compound 109 after flash chromatography (1:1 hexanes: ethyl acetate) and recrystallization from ethyl acetate hexanes. $^1$H NMR (500 MHz, CDCl$_3$) δ 9.70 (broad s, 1H), 7.65 (dd, J=7.8, 1.9, 1H), 7.43 (dd, J=7.8, 1.9, 1H), 7.24 (dd, J=7.8, 7.8, 1H), 7.18 (d, J=8.3, 1H), 6.92 (d, J=8.3, 1H), 3.78 (s, 3H), 2.00 (s, 3H), 1.97 (s, 3H).

Example 10

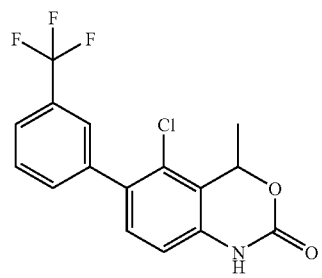

(±)-5-Chloro-1,4-dihydro-4-methyl-6-[3-(trifluoromethyl)phenyl]-2H-3,1-benzoxazin-2-one (Compound 110, Structure 6 of Scheme II)

(2-Amino-6-chlorophenyl)methanol (Structure 9 of Scheme II)

To prepare this compound, lithium aluminum hydride (3.3 g, 88 mmol) was added in three portions to a suspension of 2-amino-6-chlorobenzoic acid (5.0 g, 29 mmol) in THF (145 mL) at 0° C. That reaction was allowed to warm to room temperature and was stirred for 2 hours. Then the reaction was quenched slowly with ethyl acetate/methanol while cooling in an ice bath. That quenched suspension was filtered, washed with ethyl acetate/methanol and filtered. The filtrate was concentrated under reduced pressure and the resultant material was purified by flash chromatography (4:1 hexanes:ethyl acetate) to afford 2.75 g (61%) of 2-(amino-6-chlorophenyl)methanol.

2-Amino-6-chlorobenzaldehyde (Structure 10 of Scheme II)

To prepare this compound, manganese dioxide (13.6 g, 157 mmol) was added to a solution of 2-(amino-6-chlorophenyl)methanol (2.75 g, 17.5 mmol) in 150 mL diethyl ether. The mixture was stirred for 0.5 hours then filtered through celite and rinsed with ethyl acetate. The filtrate was concentrated under reduced pressure to afford 2.62 g (96%) of 2-amino-6-chlorobenzaldehyde.

(±)-(2-Amino-6-chlorophenyl)ethanol (Structure 3 of Scheme II)

This compound was prepared using General Method 1 (EXAMPLE 1) from 2-amino-6-chlorobenzaldehyde (45 mg, 0.29 mmol) and methylmagnesium bromide (3 M in ether, 0.24 mL) to afford (±)-(2-amino-6-chlorophenyl)ethanol after flash chromatography (4:1 hexanes:ethyl acetate).

(±)-5-Chloro-1,4-dihydro-4-methyl-2H-3,1-benzoxazin-2-one (Structure 4 of Scheme II)

This compound was prepared using General Method 2 (EXAMPLE 1) from (2-amino-6-chlorophenyl)ethanol to afford (±)-5-chloro-1,4-dihydro-4-methyl-2H-3,1-benzoxazin-2-one.

(±)-6-Bromo-5-chloro-1,4-dihydro-4-methyl-2H-3,1-benzoxazin-2-one (Structure 5 of Scheme II)

This compound was prepared using General Method 3 (EXAMPLE 1) from (±)-5-chloro-1,4-dihydro-4-methyl-2H-3,1-benzoxazin-2-one to afford (±)-6-bromo-5-chloro-1,4-dihydro-4-methyl-2H-3,1-benzoxazin-2-one.

(±)-5-Chloro-1,4-dihydro-4-methyl-6-[3-(trifluoromethyl)phenyl]-2H-3,1-benzoxazin-2-one (Compound 110, Structure 6 of Scheme II)

Compound 110 was prepared using General Method 4 (EXAMPLE 1) from (±)-6-bromo-5-chloro-1,4-dihydro-4-methyl-2H-3,1-benzoxazin-2-one and 3-(trifluoromethyl)phenylboronic acid to afford Compound 110 after flash chromatography (2:1 hexanes:ethyl acetate). $^1$H NMR (400 MHz, CDCl$_3$) δ 9.00 (broad s, 1H), 7.63 (s, 1H), 7.54 (m, 3H), 7.24 (d, J=8.2, 1H), 6.86 (d, J=8.2, 1H), 5.83 (q, J=6.7, 1H), 1.67 (d, J=6.7, 3H).

Example 11

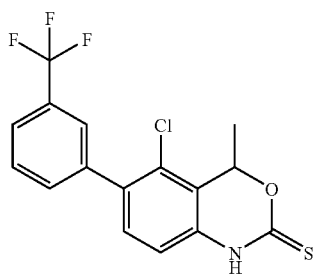

(±)-5-Chloro-1,4-dihydro-4-methyl-6-[3-(trifluoromethyl)phenyl]-2H-3,1-benzoxazin-2-thione (Compound 111, Structure 8 of Scheme II)

Compound 111 was prepared using General Method 5 (EXAMPLE 4) from Compound 110 (EXAMPLE 10) (9 mg, 0.026 mmol) to afford 4 mg (43%) of Compound 111 after flash chromatography (4:1 hexanes:ethyl acetate). $^1$H NMR (400 MHz, CDCl$_3$) δ 9.05 (broad s, 1H), 7.64 (m, 1H), 7.62 (s, 1H), 7.56 (m, 2H), 7.28 (d, J=8.2, 1H), 6.82 (d, J=8.2, 1H), 5.90 (q, J=6.7, 1H), 1.67 (d, J=6.7, 3H).

Example 12

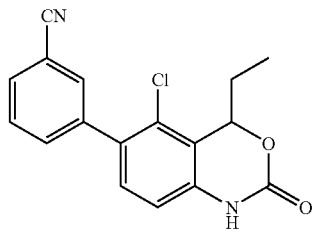

(±)-5-Chloro-6-(3-cyanophenyl)-4-ethyl-1,4-dihydro-2H-3,1-benzoxazin-2-one (Compound 112, Structure 6 of Scheme II)

(±)-1-(2-Amino-6-chlorophenyl)propan-1-ol (Structure 3 of Scheme II)

This compound was prepared using General Method 1 (EXAMPLE 1) from 2-amino-6-chlorobenzaldehyde (0.30 g, 1.9 mmol) and ethyl magnesium bromide (3 M in diethyl ether, 1.3 mL) to afford 0.17 g (48%) of (±)-1-(2-amino-6-chlorophenyl)propan-1-ol after flash chromatography (4:1 hexanes:ethyl acetate).

(±)-5-Chloro-4-ethyl-1,4-dihydro-2H-3,1-benzoxazin-2-one (Structure 4 of Scheme II)

This compound was prepared using General Method 2 (EXAMPLE 1) from (±)-1-(2-amino-6-chlorophenyl)propan-1-ol (0.18 g, 0.94 mmol) to afford 0.14 g (73%) of (±)-5-chloro-4-ethyl-1,4-dihydro-2H-3,1-benzoxazin-2-one after flash chromatography (4:1 hexanes:ethyl acetate).

(±)-6-Bromo-5-chloro-4-ethyl-1,4-dihydro-2H-3,1-benzoxazin-2-one (Structure 5 of Scheme II)

This compound was prepared using General Method 3 (EXAMPLE 1) from (±)-5-chloro-4-ethyl-1,4-dihydro-2H-3,1-benzoxazin-2-one (0.14 g, 0.68 mmol) to afford 0.16 g (84%) of (±)-6-bromo-5-chloro-4-ethyl-1,4-dihydro-2H-3,1-benzoxazin-2-one after flash chromatography (4:1 hexanes:ethyl acetate).

(±)-5-Chloro-6-(3-cyanophenyl)-4-ethyl-1,4-dihydro-2H-3,1-benzoxazin-2-one (Compound 112, Structure 6 of Scheme II)

Compound 112 was prepared using General Method 4 (EXAMPLE 1) from (±)-6-bromo-5-chloro-4-ethyl-1,4-dihydro-2H-3,1-benzoxazin-2-one (80 mg, 0.27 mmol) and 3-cyanophenylboronic acid (81 mg, 0.55 mol) to afford 70 mg (81%) of Compound 112 after flash chromatography (3:2 hexanes:ethyl acetate). $^1$H NMR (400 MHz, CDCl$_3$) δ 9.84 (s, 1H), 7.63-7.70 (m, 3H), 7.55 (t, J=7.7, 1H), 7.22 (d, J=8.2, 1H), 6.95 (d, J=8.2, 1H), 5.65 (dd, J=4.2, J=8.6, 1H), 2.00-2.05 (m, 2H), 1.17 (t, J=7.4, 3H).

Example 13

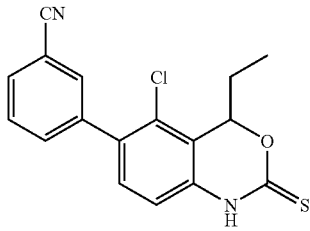

(±)-5-Chloro-6-(3-cyanophenyl)-4-ethyl-1,4-dihydro-2H-3,1-benzoxazin-2-thione (Compound 113, Structure 8 of Scheme II)

Compound 113 was prepared using General Method 5 (EXAMPLE 4) from Compound 112 (EXAMPLE 12) (40 mg, 0.13 mmol) to afford 11 mg (28%) of Compound 113. $^1$H NMR (400 MHz, CDCl$_3$) δ 9.93 (s, 1H), 7.69-7.71 (m, 2H), 7.63 (d, J=7.9, 1H), 7.57 (t, J=8.0, 1H), 7.27 (d, J=8.2, 1H) 6.93 (d, J=8.2, 1H), 5.73 (dd, J=4.2, J=8.8, 1H), 1.99-2.05 (m, 2H), 1.18 (t, J=7.4, 3H).

Example 14

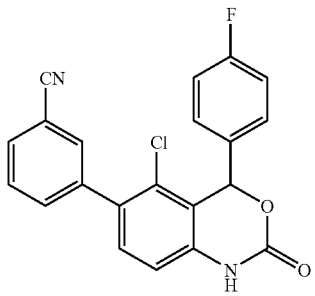

(±)-5-Chloro-6-(3-cyanophenyl)-4-(4-fluorophenyl)-1,4-dihydro-2H-3,1-benzoxazin-2-one (Compound 114, Structure 6 of Scheme II)

(±)-(2-Amino-6-chlorophenyl)-(4-fluorophenyl)methanol (Structure 3 of Scheme II)

This compound was prepared using General Method 1 (EXAMPLE 1) from 2-amino-6-chlorobenzaldehyde (0.30 g, 1.9 mmol) and 4-fluorophenylmagnesium bromide (1 M in THF, 3.8 mL) to afford 0.28 g (57%) of (±)-(2-amino-6-chlorophenyl)-(4-fluorophenyl)methanol after flash chromatography (4:1 hexanes:ethyl acetate).

(±)-5-Chloro-4-(4-fluorophenyl)-1,4-dihydro-2H-3,1-benzoxazin-2-one (Structure 4 of Scheme II)

This compound was prepared using General Method 2 (EXAMPLE 1) from (±)-1-(2-amino-6-chlorophenyl)-(4-fluorophenyl)methanol (0.28 g, 1.1 mmol) to afford 0.14 g (45%) of (±)-5-chloro-4-(4-fluorophenyl)-1,4-dihydro-2H-3,1-benzoxazin-2-one after flash chromatography (4:1 hexanes:ethyl acetate).

(±)-6-Bromo-5-chloro-4-(4-fluorophenyl)-1,4-dihydro-2H-3,1-benzoxazin-2-one (Structure 5 of Scheme II)

This compound was prepared using General Method 3 (EXAMPLE 1) from (±)-5-chloro-4-(4-fluorophenyl)-1,4-dihydro-2H-3,1-benzoxazin-2-one (0.14 g, 0.50 mmol) to afford 0.15 g of (±)-6-bromo-5-chloro-4-(4-fluorophenyl)-1,4-dihydro-2H-3,1-benzoxazin-2-one after flash chromatography (4:1 hexanes:ethyl acetate). The material could not be separated from small amounts of starting material and by-products.

(±)-5-Chloro-6-(3-cyanophenyl)-4-(4-fluorophenyl)-1,4-dihydro-2H-3,1-benzoxazin-2-one (Compound 114, Structure 6 of Scheme II)

Compound 114 was prepared using General Method 4 (EXAMPLE 1) from (±)-6-bromo-5-chloro-4-(4-fluorophenyl)-1,4-dihydro-2H-3,1-benzoxazin-2-one (80 mg, 0.22 mmol) and 3-cyanophenylboronic acid (65 mg, 0.44 mol) to afford 42 mg (51%) of Compound 114 after flash chromatography (4:1 hexanes:ethyl acetate). $^1$H NMR (400 MHz, CDCl$_3$) δ 8.08 (s, 1H), 7.64-7.71(m, 3H), 7.56 (t, J=7.7, 1H), 7.28-7.34(m, 3H), 7.07 (t, J=8.5, 2H), 6.92 (d, J=8.3, 1H), 6.69 (s, 1H).

Example 15

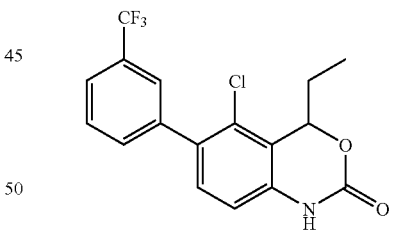

(±)-5-Chloro-4-ethyl-1,4-dihydro-6-[3-(trifluoromethyl)phenyl]-2H-3,1-benzoxazin-2-one (Compound 115, Structure 6 of Scheme II)

Compound 115 was prepared using General Method 4 (EXAMPLE 1) from (±)-6-bromo-5-chloro-4-ethyl-1,4-dihydro-2H-3,1-benzoxazin-2-one (72 mg, 0.25 mmol) and 3-(trifluoromethyl)phenylboronic acid to afford 71 mg (81%) of Compound 115 after flash chromatography (4:1 hexanes: ethyl acetate). $^1$H NMR (400 MHz, CDCl$_3$) δ 8.20 (s, 1H), 7.60-7.65 (m, 2H), 7.50-7.60 (m, 2H), 7.25 (d, J=8.2, 1H), 6.83 (d, J=8.1, 1H), 5.70 (dd, J=4.2, J=8.7, 1H), 1.98-2.01(m, 2H), 1.16 (t, J=7.4, 3H).

Example 16

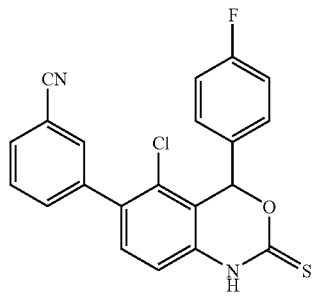

(±)-5-Chloro-6-(3-cyanophenyl)-4-(4-fluorophenyl)-
1,4-dihydro-2H-3,1-benzoxazin-2-thione (Compound 116, Structure 8 of Scheme II)

Compound 116 was prepared using General Method 5 (EXAMPLE 4) from Compound 114 (EXAMPLE 14) (25 mg, 0.066 mmol) to afford 14 mg (54%) of Compound 116. $^1$H NMR (400 MHz, CDCl$_3$) δ 10.0 (broad s, 1H), 7.71 (m, 2H), 7.69-7.70 (m, 1H), 7.56 (t, J=8.2, 1H), 7.37 (d, J=8.2, 1H), 7.28-7.32 (m, 2H), 7.04-7.09 (m, 2H), 7.02 (d, J=8.3, 1H), 6.77 (s, 1H).

Example 17

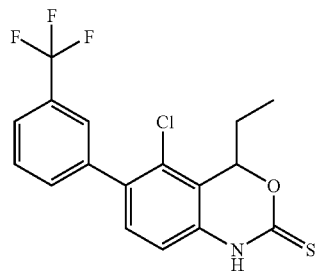

(±)-5-Chloro-4-ethyl-1,4-dihydro-6-[3-(trifluoromethyl)phenyl]-2H-3,1-benzoxazin-2-thione (Compound 117, Structure 8 of Scheme II)

Compound 117 was prepared using General Method 5 (EXAMPLE 4) from Compound 115 (EXAMPLE 15) (52 mg, 0.15 mmol) to afford 24 mg (43%) of Compound 117. $^1$H NMR (400 MHz, CDCl$_3$) δ 10.3 (s, 1H), 7.62-7.70 (m, 2H), 7.55-7.60 (m, 2H), 7.30 (d, J=8.2, 1H), 6.97 (d, J=8.2, 1H), 5.75 (dd, J=4.2, J=8.7, 1H), 2.00-2.06 (m, 2H), 1.18 (t, J=7.4, 3H).

Example 18

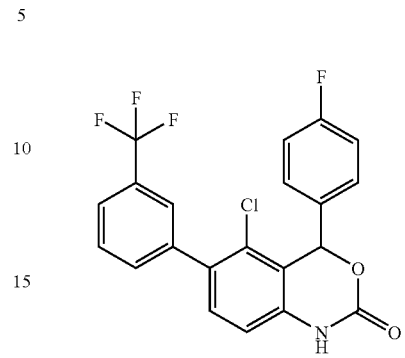

(±)-5-Chloro-4-(4-fluorophenyl)-1,4-dihydro-6-[3-(trifluoromethyl)phenyl]-2H-3,1-benzoxazin-2-one (Compound 118, Structure 6 of Scheme II)

Compound 118 was prepared using General Method 4 (EXAMPLE 1) from (±)-6-bromo-5-chloro-4-(4-fluorophenyl)-1,4-dihydro-2H-3,1-benzoxazin-2-one (67 mg, 0.19 mmol) and 3-(trifluoromethyl)phenylboronic acid to afford 65 mg of a white solid after flash chromatography (4:1 hexanes:ethyl acetate). Further purification by HPLC (reverse phase ODS, 80% methanol:water) afforded Compound 118. $^1$H NMR (500 MHz, CDCl$_3$) δ 9.16 (s, 1H), 7.63-7.70 (m, 2H), 7.55-7.62 (m, 2H), 7.34 (d, J=8.3, 1H), 7.29-7.32 (m, 2H), 7.06 (t, J=8.5, 2H), 6.96 (d, J=8.2, 1H), 6.70 (s, 1H).

Example 19

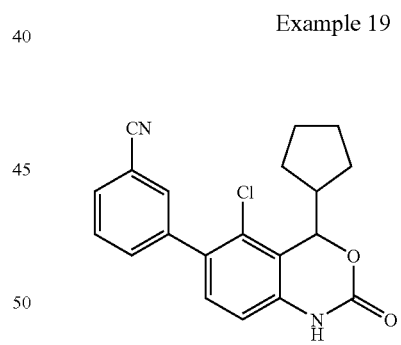

(±)-5-Chloro-6-(3-cyanophenyl)-4-cyclopentyl-1,4-dihydro-2H-3,1-benzoxazin-2-one (Compound 119, Structure 6 of Scheme II)

(±)-(2-Amino-6-chlorophenyl)-cyclopentyl-methanol (Structure 3 of Scheme II)

This compound was prepared using General Method 1 (EXAMPLE 1) from 2-amino-6-chlorobenzaldehyde (0.30 g, 1.9 mmol) and cyclopentylmagnesium bromide (2 M in ether, 1.9 mL)) to afford 0.16 g (36%) of (±)-(2-amino-6-chlorophenyl)-cyclopentyl-methanol after flash chromatography (4:1 hexanes:ethyl acetate).

(±)-5-Chloro-4-cyclopentyl-1,4-dihydro-2H-3,1-benzoxazin-2-one (Structure 4 of Scheme II)

This compound was prepared using General Method 2 (EXAMPLE 1) from (±)-1-(2-amino-6-chlorophenyl)-cyclopentyl-methanol (0.28 g, 1.1 mmol) to afford 0.10 g (60%) of (±)-5-chloro-4-cyclopentyl-1,4-dihydro-2H-3,1-benzoxazin-2-one after flash chromatography (4:1 hexanes:ethyl acetate).

(±)-6-Bromo-5-chloro-4-cyclopentyl-1,4-dihydro-2H-3,1-benzoxazin-2-one (Structure 5 of Scheme II)

This compound was prepared using General Method 3 (EXAMPLE 1) from (±)-5-chloro-4-cyclopentyl-1,4-dihydro-2H-3,1-benzoxazin-2-one (0.10 g, 0.40 mmol) to afford 55 mg (34%) of (±)-6-bromo-5-chloro-4-cyclopentyl-1,4-dihydro-2H-3,1-benzoxazin-2-one after flash chromatography (4:1 hexanes:ethyl acetate).

(±)-5-Chloro-6-(3-cyanophenyl)-4-cyclopentyl-1,4-dihydro-2H-3,1-benzoxazin-2-one (Compound 119, Structure 6 of Scheme II)

Compound 119 was prepared using General Method 4 (EXAMPLE 1) from (±)-6-bromo-5-chloro-4-cyclopentyl-1,4-dihydro-2H-3,1-benzoxazin-2-one (55 mg, 0.17 mmol) and 3-cyanophenylboronic acid (49 mg, 0.33 mmol) to afford 30 mg (52%) of Compound 119. $^1$H NMR (500 MHz, CDCl$_3$) δ 9.65 (s, 1H), 7.65-7.71 (m, 2H), 7.60-7.65 (m, 1H), 7.54 (t, J=7.6, 1H), 7.21 (d, J=8.0, 1H), 6.93 (d, J=8.3, 1H), 5.65 (d, J=6.7, 1H), 2.51-2.55 (m, 1H), 1.57-1.86 (m, 8H).

Example 20

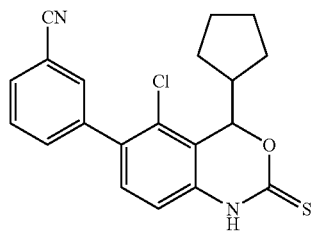

(±)-5-Chloro-6-(3-cyanophenyl)-4-cyclopentyl-1,4-dihydro-2H-3,1-benzoxazin-2-thione (Compound 120, Structure 8 of Scheme II)

Compound 120 was prepared using General Method 5 (EXAMPLE 4) from Compound 119 (EXAMPLE 19) (20 mg, 0.056 mmol) to afford 10 mg (48%) of Compound 120. $^1$H NMR (500 MHz, CDCl$_3$) δ 9.64 (s, 1H), 7.68-7.74 (m, 2H), 7.60-7.65 (m, 1H), 7.52-7.60 (m, 1H), 7.27 (d, J=8.5, 1H), 6.9 (d, J=8.0, 1H), 5.71 (d, J=7.3, 1H), 2.48-2.54 (m, 1H), 1.56-1.78 (m, 8H).

Example 21

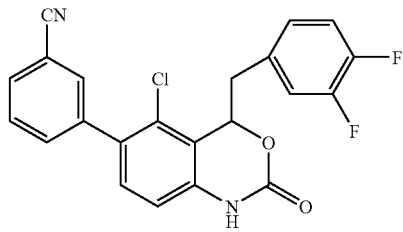

(±)-5-Chloro-6-(3-cyanophenyl)-4-(3,4-difluorobenzyl)-1,4-dihydro-2H-3,1-benzoxazin-2-one (Compound 121, Structure 6 of Scheme II)

(±)-1-(2-Amino-6-chlorophenyl)-2-(3,4-difluorophenyl)ethanol (Structure 3 of Scheme II)

This compound was prepared using General Method 1 (EXAMPLE 1) from 2-amino-6-chlorobenzaldehyde (0.30 g, 1.9 mmol) and 3,4-difluorobenzylmagnesium bromide (generated from 3,4-difluorobenzyl bromide and magnesium in ether, 3.9 mmol, 2 equiv) to afford 0.28 g (57%) of (±)-1-(2-amino-6-chlorophenyl)-2-(3,4-difluorophenyl)ethanol after flash chromatography (4:1 hexanes:ethyl acetate).

(±)-5-Chloro-4-(3,4-difluorobenzyl)-1,4-dihydro-2H-3,1-benzoxazin-2-one (Structure 4 of Scheme II)

This compound was prepared using General Method 2 (EXAMPLE 1) from (±)-1-(2-amino-6-chlorophenyl)-2-(3,4-difluorophenyl)ethanol (0.28 g, 1.1 mmol) to afford 0.21 g (64%) of (±)-5-chloro-4-(3,4-difluorobenzyl)-1,4-dihydro-2H-3,1-benzoxazin-2-one after flash chromatography (4:1 hexanes:ethyl acetate).

(±)-6-Bromo-5-chloro-4-(3,4-difluorobenzyl)-1,4-dihydro-2H-3,1-benzoxazin-2-one (Structure 5 of Scheme II)

This compound was prepared using General Method 3 (EXAMPLE 1) from (±)-5-chloro-4-(3,4-difluorobenzyl)-1,4-dihydro-2H-3,1-benzoxazin-2-one (0.21 g, 0.69 mmol) to afford 0.21 g of (±)-6-bromo-5-chloro-4-(3,4-difluorobenzyl)-1,4-dihydro-2H-3,1-benzoxazin-2-one after flash chromatography (4:1 hexanes:ethyl acetate).

(±)-5-Chloro-6-(3-cyanophenyl)-4-(3,4-difluorobenzyl)-1,4-dihydro-2H-3,1-benzoxazin-2-one (Compound 121, Structure 6 of Scheme II)

Compound 121 was prepared using General Method 4 (EXAMPLE 1) from (±)-6-bromo-5-chloro-4-(3,4-difluorobenzyl)-1,4-dihydro-2H-3,1-benzoxazin-2-one (210 mg, 0.54 mmol) and 3-cyanophenylboronic acid (0.24 g, 1.6 mmol) to afford 42 mg (51%) of 0.14 g (64%) of Compound 121 after flash chromatography (3:1 hexanes:ethyl acetate). $^1$H NMR (500 MHz, CDCl$_3$) δ 9.26(s, 1H), 7.70-7.71 (m, 2H), 7.64-7.66 (m, 1H), 7.58 (t, J=8.0, 1H), 7.27 (d, J=8.0, 1H), 7.07-7.12 (m, 1H), 6.99-7.03 (m, 1H), 6.91-6.94 (m, 1H), 6.88 (d, J=8.2, 1H), 5.88 (dd, J=4.5, J=7.5, 1H), 3.19-3.14-3.24 (m, 2H).

Example 22

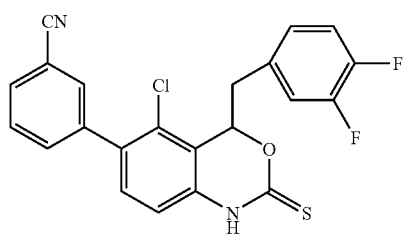

(±)-5-Chloro-6-(3-cyanophenyl)-4-(3,4-difluorobenzyl)-1,4-dihydro-2H-3,1-benzoxazin-2-thione (Compound 122, Structure 8 of Scheme II)

Compound 122 was prepared using General Method 5 (EXAMPLE 4) from Compound 121 (EXAMPLE 21) (9 mg, 0.026 mmol) to afford 4 mg (43%) of Compound 122 after flash chromatography (4:1 hexanes:ethyl acetate). $^1$H NMR (500 MHz, CDCl$_3$) δ 10.07 (s, 1H), 7.70-7.73 (m, 2H), 7.57-7.65 (m, 2H), 7.25-7.32 (m, 1H), 7.04-7.12 (m, 2H), 6.96-6.98 (m, 1H), 6.92-6.93 (m, 1H), 5.92 (dd, J=3.5, J=8.0, 1H), 3.13-3.21 (m, 2H).

Example 23

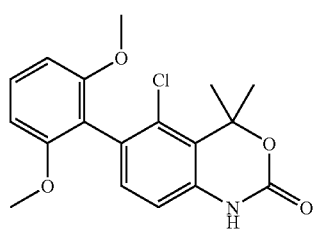

5-Chloro-1,4-dihydro-6-(2,6-dimethoxyphenyl)-4,4-dimethyl-2H-3,1-benzoxazin-2-one (Compound 123, Structure 6 of Scheme I)

Compound 123 was prepared according to General Method 4 (EXAMPLE 1) from 6-bromo-5-chloro-1,4-dihydro-4,4-dimethyl-2H-3,1-benzoxazin-2-one (29 mg) and 2,6-dimethoxyphenylboronic acid (27 mg) to afford 5 mg (14%) of compound 123. $^1$H NMR (400 MHz, CDCl$_3$) δ 8.74 (s, 1H), 7.33 (dd, J=8.5, 8.2, 1H), 7.09 (d, J=7.9, 1H), 6.80 (d, J=8.2, 1H), 6.64 (d, J=8.5, 1H), 3.74 (s, 6H), 1.96 (s, 6H).

Example 24

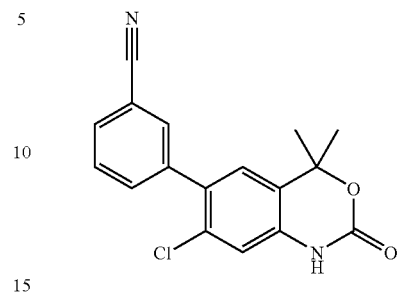

7-Chloro-6-(3-cyanophenyl)-1,4-dihydro-4,4-dimethyl-2H-3,1-benzoxazin-2-one (Compound 124, Structure 6 of Scheme I)

2-(2-Amino-4-chlorophenyl)propan-2-ol (Structure 3 of Scheme I)

This compound was prepared using General Method 1 (EXAMPLE 1) from methyl 2-amino-4-chlorobenzoate (2.8 g) and methyl magnesium bromide (3 M in diethyl ether, 20 mL) in 75 mL ether to afford 2-(2-amino-4-chlorophenyl)propan-2-ol.

7-Chloro-1,4-dihydro-4,4-dimethyl-2H-3,1-benzoxazin-2-one (Structure 4 of Scheme I)

This compound was prepared using General Method 2 (EXAMPLE 1) from 2-(2-amino-4-chlorophenyl)propan-2-ol (2.7) to afford 1.3 g (36%) of 7-chloro-1,4-dihydro-4,4-dimethyl-2H-3,1-benzoxazin-2-one, an off-white solid.

6-Bromo-7-chloro-1,4-dihydro-4,4-dimethyl-2H-3,1-benzoxazin-2-one (Structure 5 of Scheme I)

This compound was prepared using General Method 3 (EXAMPLE 1) from 7-chloro-1,4-dihydro-4,4-dimethyl-2H-3,1-benzoxazin-2-one (212 mg) to afford 86 mg (85%) of 6-bromo-7-chloro-1,4-dihydro-4,4-dimethyl-2H-3,1-benzoxazin-2-one, a white solid, after recrystallization from EtOAc/hexanes.

7-Chloro-6-(3-cyanophenyl)-1,4-dihydro-4,4-dimethyl-2H-3,1-benzoxazin-2-one (Compound 124, Structure 6 of Scheme I)

Compound 124 was prepared using General Method 4 (EXAMPLE 1) from 6-bromo-7-chloro-1,4-dihydro-4,4-dimethyl-2H-3,1-benzoxazin-2-one (43 mg) and 3-cyanophenylboronic acid (31 mg) to afford 29 mg (62%) of compound 125. $^1$H NMR (400 MHz, Acetone-d$_6$) δ 9.4 (broad s, 1H), 7.80-7.95 (m, 3H), 7.70 (t, J=7.7, 1H), 7.46 (s, 1H), 7.19 (s, 1H), 1.72 (s, 6H).

Example 25

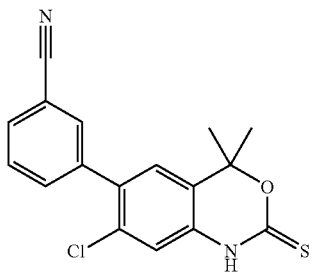

7-Chloro-6-(3-cyanophenyl)-1,4-dihydro-4,4-dimethyl-2H-3,1-benzoxazin-2-thione (Compound 125, Structure 8 of Scheme I)

Compound 125 was prepared using General Method 5 (EXAMPLE 4) from Compound 124 (16 mg) to afford Compound 125 after flash chromatography (4:1 hexanes:ethyl acetate). $^1$H NMR (400 MHz, CDCl$_3$) δ 9.51 (s, 1H), 7.65-7.75 (m, 2H), 7.57 (t, J=8.0, 1H), 7.09 (s, 1H), 7.04 (s, 1H), 1.79 (s, 6H).

Example 26

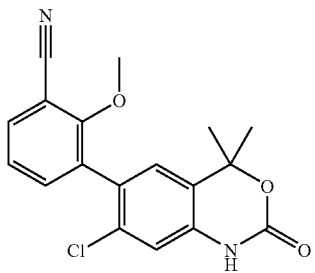

7-Chloro-6-(3-cyano-2-methoxyphenyl)-1,4-dihydro-4,4-dimethyl-2H-3,1-benzoxazin-2-one (Compound 126, Structure 6 of Scheme I)

Compound 126 was prepared using General Method 4 (EXAMPLE 1) from 6-bromo-7-chloro-1,4-dihydro-4,4-dimethyl-2H-3,1-benzoxazin-2-one (44 mg) and 2-methoxy-3-(4,4,5,5-tetramethyl-1,3,2-dioxaborolan-2-yl)benzonitrile (47 mg) to afford 37 mg (73%) of compound 126. $^1$H NMR (400 MHz, CDCl$_3$) δ 8.81 (s, 1H), 7.64 (dd, J=7.9, 1.8, 1H), 7.47 (dd, J=7.6, 1.7, 1H), 7.23 (t, J=7.6, 1H), 7.09 (s, 1H), 7.04 (s, 1H), 3.74 (s, 3H), 1.74 (s, 6H).

Example 27

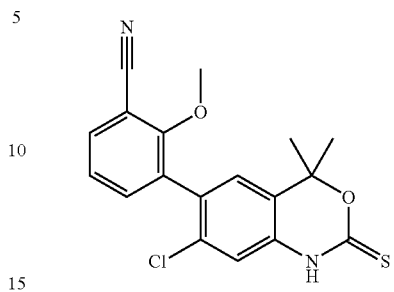

7-Chloro-6-(3-cyano-2-methoxyphenyl)-1,4-dihydro-4,4-dimethyl-2H-3,1-benzoxazin-2-thione (Compound 127, Structure 8 of Scheme 1)

Compound 127 was prepared using General Method 5 (EXAMPLE 4) from Compound 126 (16 mg) to afford Compound 127 (8.2 mg, 48%). $^1$H NMR (400 MHz, CDCl$_3$) δ 10.1 (s, 1H), 7.66 (dd, J=7.7, 1.6, 1H), 7.46 (dd, J=7.5, 1.7, 1H), 7.24 (t, J=7.8, 1H), 7.11 (s, 1H), 7.10 (s, 1H), 3.76 (s, 3H). 1.77 (s, 6H).

Example 28

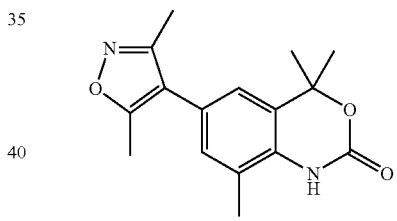

6-(3,5-Dimethylisoxazol-4-yl)-1,4-dihydro-4,4,8-trimethyl-2H-3,1-benzoxazin-2-one (Compound 128, Structure 6 of Scheme I)

2-(2-Amino-4-methylphenyl)propan-2-ol (Structure 3 of Scheme I)

This compound was prepared using General Method 1 (EXAMPLE 1) from methyl 2-amino-3-methylbenzoate and methyl magnesium bromide (3 M in diethyl ether) in ether to afford 2-(2-amino-3-methylphenyl)propan-2-ol.

1,4-Dihydro-4,4,8-trimethyl-2H-3,1-benzoxazin-2-one (Structure 4 of Scheme I)

This compound was prepared using General Method 2 (EXAMPLE 1) from 2-(2-amino-3-methylphenyl)propan-2-ol to afford 1,4-dihydro-4,4,8-trimethyl-2H-3,1-benzoxazin-2-one.

6-Bromo-1,4-dihydro-4,4,8-trimethyl-2H-3,1-benzoxazin-2-one (Structure 5 of Scheme I)

This compound was prepared using General Method 3 (EXAMPLE 1) from 1,4-dihydro-4,4,8-trimethyl-2H-3,1-benzoxazin-2-one to afford 6-bromo-1,4-dihydro-4,4,8-trimethyl-2H-3,1-benzoxazin-2-one.

6-(3,5-Dimethylisoxazol-4-yl)-1,4-dihydro-4,4,8-trimethyl-2H-3,1-benzoxazin-2-one (Compound 128, Structure 6 of Scheme I)

Compound 128 was prepared using General Method 4 (EXAMPLE 1) from 6-bromo-1,4-dihydro-4,4,8-trimethyl-2H-3,1-benzoxazin-2-one and 3,5-dimethylisoxazol-4-ylboronic acid to afford compound 128. $^1$H NMR (500 MHz, CDCl$_3$) δ 8.04 (broad s, 1H), 6.99 (d, J=1.0, 1H), 6.88 (s, 1H), 2.40 (s, 3H), 2.35 (s, 3H), 2.25 (s, 3H), 1.75 (s, 6H).

Example 29

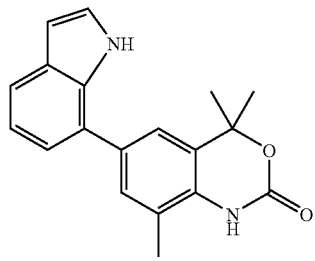

1,4-Dihydro-6-(indol-7-yl)-4,4,8-trimethyl-2H-3,1-benzoxazin-2-one (Compound 129, Structure 6 of Scheme I)

7-(4,4,5,5-tetramethyl-1,32-dioxaborolan-2-yl)indole

This compound was prepared by combining a mixture of 7-bromoindole (5.9 g), Pd(dppf)Cl$_2$ dichloromethane complex (0.98 g, 1.2 mmol) in a flask and flushing the flask with nitrogen. Then dioxane (140 mL), triethylamine (14.6 mL), and pinacolborane (8.0 mL) is added. The reaction is heated at 100° C. for 18 h. The reaction is quenched with saturated ammonium chloride, and the mixture is extracted with EtOAc (2×250 mL). The organic layers is washed with brine, dried over magnesium sulfate, filtered, and concentrated. Flash chromatography (15% EtOAc/hexanes) affords 7-(4,4,5,5-tetramethyl-1,3,2-dioxaborolan-2-yl)indole (5.5 g).

1,4-Dihydro-6-(indol-7-yl)-4,4,8-trimethyl-2H-3,1-benzoxazin-2-one (Compound 129, Structure 6 of Scheme I)

Compound 129 was prepared using General Method 4 (EXAMPLE 1) from 6-bromo-1,4-dihydro-4,4,8-trimethyl-2H-3,1-benzoxazin-2-one (40 mg) and 7-(4,4,5,5-tetramethyl-1,3,2-dioxaborolan-2-yl)indole (40 mg) to afford compound 129 (34 mg, 74%). $^1$H NMR (500 MHz, CDCl$_3$) δ 8.36 (s, 1H), 8.07 (s, 1H), 7.64 (d, J=7.7 Hz, 1H), 7.40 (d, J=1.6 Hz, 1H), 7.26-7.24 (m, 2H), 7.20 (dd, J=7.7, 7.2 Hz, 1H), 7.15 (d, J=7.2 Hz, 1H), 6.64 (dd, J=3.0, 2.0 Hz, 1H), 2.39 (s, 3H), 1.77 (s, 6H).

Example 30

Mineralocorticoid Binding Assays
Preparation of MR

A baculovirus expression plasmid comprising cDNA encoding the human mineralocorticoid receptor protein (MR) was prepared using standard techniques. See e.g. E. A. Allegretto et. al. 268 *J. Biol. Chem.*, 26625 (1993); G. Srinivasan and B. Thompson, 4 *Mol. Endo.*, 209 (1990); and D. R. O'Reilly et. al., in "Baculovirus Expression Vectors", D. R. O'Reilly et. al., eds., W. H. Freeman, New York, N.Y., pp. 139-179 (1992). That expression plasmid was co-transfected together with wild type *Autographa californica* multiple nuclear polyhedrosis virus DNA into *Spodoptera frugiperda*-21 (Sf-21) cells to generate recombinant virus comprising MR cDNA. See e.g. O'Reilly, D. R., Miller, L. K., Luckow, V. A., Regulation of expression of a baculovirus ecdysteroid UDP glucosyltransferase gene. "Baculovirus Expression Vectors." WH Freeman, NY, 139-179 (1992). That recombinant virus comprising MR cDNA was collected.

A suspension culture of uninfected Sf21 cells was grown to a density of 1.2×10$^6$ cells/ml and then infected with the recombinant virus comprising MR cDNA at a multiplicity of infection of 2. Those infected Sf21 cells were incubated for 48 hours and then collected by centrifugation at 1000×g for 10 minutes at 4° C. The resulting cell pellets were resuspended in lysis buffer (50 mM Potassium Phosphate buffer, pH 7.0, 10 mM Monothioglycerol, 5 mM DTT, 20 mM Sodium Molybdate, 1 mM PMSF, 1 µg/mL aprotinin, and 10 µg/mL leupeptin) and incubated for 15 minutes on ice. Those resuspended cell pellets were homogenized using a Dounce homogenizer and a B pestle. A volume of 2 M KCl was added to the homogenized cell pellets to a final concentration of 0.4 M. The resulting MR lysates were centrifuged at 100,000×g for 60 min at 4° C. and stored for use in binding assays.

Binding Assays

Binding assay samples were prepared in separate minitubes in a 96-well format at 4° C. Each binding assay sample was prepared in a volume of 250 µl of MR-Assay Buffer (10% glycerol, 10 mM sodium phosphate, 10 mM potassium fluoride, 20 mM sodium molybdate, 0.25 mM CHAPS, 2 mM DTT, (adjusted to pH 7.35)) containing 5-10 µg of MR lysate; 2-4 nM of [$^3$H]aldosterone; unlabeled aldosterone; and a test compound. Each test compound was assayed at several different concentrations, ranging from 0 to 10$^{-5}$ M and each was tested in the presence and in the absence of several different concentrations of unlabeled aldosterone. Each concentration of each test compound was assayed in triplicate. The assay samples were incubated for 16 hours at 4° C.

After incubation, 200 µl of 6.25% hydroxylapatite in assay buffer was added to each assay sample to precipitate the protein. The assay samples were then centrifuged and the supernatants were discarded. The resulting pellets were washed twice with assay buffer lacking DTT. Radioactivity in counts per minute (CPM) of each washed pellet was determined by liquid scintillation counter (MicroBeta™, Wallach).

Specific binding for a particular sample was calculated using the equation:

(Sample CPM)−(Average Non-specific CPM)

Average Non-specific CPM was defined as the amount of radioactivity from samples comprising an excess (i.e. 1000 nM) of unlabeled aldosterone. IC$_{50}$ values (the concentration of test compound required to decrease specific binding by 50%) were determined using the log-logit (Hill) method. K$_i$ values were determined using the Cheng-Prusoff equation using a previously determined $K_d$ value for aldosterone:

$$K_i = IC_{50}/(1+[L]/K_d)$$

[L]=concentration of labeled aldosterone $K_d$=dissociation constant of labeled aldosterone $K_i$ values for certain mineralocorticoid receptor binding compounds are shown in Table 1.

TABLE 1

MR Binding Data

| Compound | $K_i$ |
|---|---|
| 101 | 98 |
| 102 | 440 |
| 103 | 375 |
| 104 | 52 |
| 111 | 45 |
| 118 | 150 |

What is claimed is:

1. A compound selected from the group consisting of:
   5-Chloro-6-(3-cyanophenyl)-1,4-dihydro-4,4-dimethyl-2H-3,1-benzoxazin-2-one (Compound 101);
   5-Chloro-1,4-dihydro-4,4-dimethyl-6-[3-(trifluoromethyl)phenyl]-2H-3,1-benzoxazin-2-one (Compound 102);
   6-(3-Acetylphenyl)-5-chloro-1,4-dihydro-4,4-dimethyl-2H-3,1-benzoxazin-2-one (Compound 103);
   5-Chloro-1,4-dihydro-4,4-dimethyl-6-[3-(trifluoromethyl)phenyl]-2H-3,1-benzoxazin-2-thione (Compound 104);
   5-Chloro-6-(3-chlorophenyl)-1,4-dihydro-4,4-dimethyl-2H-3,1-benzoxazin-2-one (Compound 105);
   5-Chloro-6-(3-cyanophenyl)-1,4-dihydro-4,4-dimethyl-2H-3,1-benzoxazin-2-thione (Compound 106);
   6-(3-Carboxymethylphenyl)-5-chloro-1,4-dihydro-4,4-dimethyl-2H-3,1-benzoxazin-2-one (Compound 107);
   5-Chloro-6-(3-cyanophenyl)-1,4-dihydro-1,4,4-trimethyl-2H-3,1-benzoxazin-2-one (Compound 108);
   5-Chloro-6-(3-cyano-2-methoxyphenyl)-1,4-dihydro-4,4-dimethyl-2H-3,1-benzoxazin-2-one (Compound 109);
   (±)-5-Chloro-1,4-dihydro-4-methyl-6-[3-(trifluoromethyl)phenyl]-2H-3,1-benzoxazin-2-one (Compound 110);
   (±)-5-Chloro-1,4-dihydro-4-methyl-6-[3-(trifluoromethyl)phenyl]-2H-3,1-benzoxazin-2-thione (Compound 111);
   (±)-5-Chloro-6-(3-cyanophenyl)-4-ethyl-1,4-dihydro-2H-3,1-benzoxazin-2-one (Compound 112);
   (±)-5-Chloro-6-(3-cyanophenyl)-4-ethyl-1,4-dihydro-2H-3,1-benzoxazin-2-thione (Compound 113);
   (±)-5-Chloro-6-(3-cyanophenyl)-4-(4-fluorophenyl)-1,4-dihydro-2H-3,1-benzoxazin-2-one (Compound 114);
   (±)-5-Chloro-4-ethyl-1,4-dihydro-6-[3-(trifluoromethyl)phenyl]-2H-3,1-benzoxazin-2-one (Compound 115);
   (±)-5-Chloro-6-(3-cyanophenyl)-4-(4-fluorophenyl)-1,4-dihydro-2H-3,1-benzoxazin-2-thione (Compound 116);
   (±)-5-Chloro-4-ethyl-1,4-dihydro-6-[3-(trifluoromethyl)phenyl]-2H-3,1-benzoxazin-2-thione (Compound 117);
   (±)-5-Chloro-4-(4-fluorophenyl)-1,4-dihydro-6-[3-(trifluoromethyl)phenyl]-2H-3,1-benzoxazin-2-one (Compound 118);
   (±)-5-Chloro-6-(3-cyanophenyl)-4-cyclopentyl-1,4-dihydro-2H-3,1-benzoxazin-2-one (Compound 119);
   (±)-5-Chloro-6-(3-cyanophenyl)-4-cyclopentyl-1,4-dihydro-2H-3,1-benzoxazin-2-thione (Compound 120);
   (±)-5-Chloro-6-(3-cyanophenyl)-4-(3,4-difluorobenzyl)-1,4-dihydro-2H-3,1-benzoxazin-2-one (Compound 121);
   (±)-5-Chloro-6-(3-cyanophenyl)-4-(3,4-difluorobenzyl)-1,4-dihydro-2H-3,1-benzoxazin-2-thione (Compound 122);
   5-Chloro-1,4-dihydro-6-(2,6-dimethoxyphenyl)-4,4-dimethyl-2H-3,1-benzoxazin-2-one (Compound 123);
   7-Chloro-6-(3-cyanophenyl)-1,4-dihydro-4,4-dimethyl-2H-3,1-benzoxazin-2-one (Compound 124);
   7-Chloro-6-(3-cyanophenyl)-1,4-dihydro-4,4-dimethyl-2H-3,1-benzoxazin-2-thione (Compound 125);
   7-Chloro-6-(3-cyano-2-methoxyphenyl)-1,4-dihydro-4,4-dimethyl-2H-3,1-benzoxazin-2-one (Compound 126);
   7-Chloro-6-(3-cyano-2-methoxyphenyl)-1,4-dihydro-4,4-dimethyl-2H-3,1-benzoxazin-2-thione (Compound 127);
   6-(3,5-Dimethylisoxazol-4-yl)-1,4-dihydro-4,4,8-trimethyl-2H-3,1-benzoxazin-2-one (Compound 128);
   1,4-Dihydro-6-(indol-7-yl)-4,4,8-trimethyl-2H-3,1-benzoxazin-2-one (Compound 129); and
   a pharmaceutically acceptable salt, ester, or amide of any of those compounds.

2. A pharmaceutical agent comprising a physiologically acceptable carrier, diluent, or excipient, or a combination thereof; and a compound of claim 1.

3. The compound of claim 1, wherein the compound is 5-Chloro-6-(3-cyanophenyl)-1,4-dihydro-4,4-dimethyl-2H-3,1-benzoxazin-2-one (Compound 101), a pharmaceutically acceptable salt thereof, an ester thereof or an amide thereof.

4. The compound of claim 1, wherein the compound is 5-Chloro-1,4-dihydro-4,4-dimethyl-6-[3-(trifluoromethyl)phenyl]-2H-3,1-benzoxazin-2-one (Compound 102), a pharmaceutically acceptable salt thereof, an ester thereof or an amide thereof.

5. The compound of claim 1, wherein the compound is 6-(3-Acetylphenyl)-5-chloro-1,4-dihydro-4,4-dimethyl-2H-3,1-benzoxazin-2-one (Compound 103), a pharmaceutically acceptable salt thereof, an ester thereof or an amide thereof.

6. The compound of claim 1, wherein the compound is 5-Chloro-1,4-dihydro-4,4-dimethyl-6-[3-(trifluoromethyl)phenyl]-2H-3,1-benzoxazin-2-thione (Compound 104), a pharmaceutically acceptable salt thereof, an ester thereof or an amide thereof.

7. The compound of claim 1, wherein the compound is 5-Chloro-6-(3-chlorophenyl)-1,4-dihydro-4,4-dimethyl-2H-3,1-benzoxazin-2-one (Compound 105), a pharmaceutically acceptable salt thereof an ester thereof or an amide thereof.

8. The compound of claim 1, wherein the compound is 5-Chloro-6-(3-cyanophenyl)-1,4-dihydro-4,4-dimethyl-2H-3,1-benzoxazin-2-thione (Compound 106), a pharmaceutically acceptable salt thereof, an ester thereof or an amide thereof.

9. The compound of claim 1, wherein the compound is 6-(3-Carboxymethylphenyl)-5-chloro-1,4-dihydro-4,4-dimethyl-2H-3,1-benzoxazin-2-one (Compound 107), a pharmaceutically acceptable salt thereof, an ester thereof or an amide thereof.

10. The compound of claim 1, wherein the compound is 5-Chloro-6-(3-cyanophenyl)-1,4-dihydro-1,4,4-trimethyl-2H-3,1-benzoxazin-2-one (Compound 108), a pharmaceutically acceptable salt thereof an ester thereof or an amide thereof.

11. The compound of claim 1, wherein the compound is 5-Chloro-6-(3-cyano-2-methoxyphenyl)-1,4-dihydro-4,4- dimethyl-2H-3,1-benzoxazin-2-one (Compound 109), a pharmaceutically acceptable salt thereof, an ester thereof or an amide thereof.

12. The compound of claim 1, wherein the compound is (±)-5-Chloro-1,4-dihydro-4-methyl-6-[3-(trifluoromethyl)phenyl]-2H-3,1-benzoxazin-2-one (Compound 110), a pharmaceutically acceptable salt thereof, an ester thereof or an amide thereof.

13. The compound of claim 1, wherein the compound is (±)-5-Chloro-1,4-dihydro-4-methyl-6-[3-(trifluoromethyl)phenyl]-2H-3,1-benzoxazin-2-thione (Compound 111), a pharmaceutically acceptable salt thereof, an ester thereof or an amide thereof.

14. The compound of claim 1, wherein the compound is (±)-5-Chloro-6-(3-cyanophenyl)-4-ethyl-1,4-dihydro-2H-3,1-benzoxazin-2-one (Compound 112), a pharmaceutically acceptable salt thereof, an ester thereof or an amide thereof.

15. The compound of claim 1, wherein the compound is (±)-5-Chloro-6-(3-cyanophenyl)-4-ethyl-1,4-dihydro-2H-3,1-benzoxazin-2-thione (Compound 113), a pharmaceutically acceptable salt thereof, an ester thereof or an amide thereof.

16. The compound of claim 1, wherein the compound is (±)-5-Chloro-6-(3-cyanophenyl)-4-(4-fluorophenyl)-1,4-dihydro-2H-3,1-benzoxazin-2-one (Compound 114), a pharmaceutically acceptable salt thereof, an ester thereof or an amide thereof.

17. The compound of claim 1, wherein the compound is (±)-5-Chloro-4-ethyl-1,4-dihydro-6-[3-(trifluoromethyl)phenyl]-2H-3,1-benzoxazin-2-one (Compound 115), a pharmaceutically acceptable salt thereof, an ester thereof or an amide thereof.

18. The compound of claim 1, wherein the compound is (±)-5-Chloro-6-(3-cyanophenyl)-4-(4-fluorophenyl)-1,4-dihydro-2H-3,1-benzoxazin-2-thione (Compound 116), a pharmaceutically acceptable salt thereof, an ester thereof or an amide thereof.

19. The compound of claim 1, wherein the compound is (±)-5-Chloro-4-ethyl-1,4-dihydro-6-[3-(trifluoromethyl)phenyl]-2H-3,1-benzoxazin-2-thione (Compound 117), a pharmaceutically acceptable salt thereof, an ester thereof or an amide thereof.

20. The compound of claim 1, wherein the compound is (±)-5-Chloro-4-(4-fluorophenyl)-1,4-dihydro-6-[3-(trifluoromethyl)phenyl]-2H-3,1-benzoxazin-2-one (Compound 118), a pharmaceutically acceptable salt thereof, an ester thereof or an amide thereof.

21. The compound of claim 1, wherein the compound is (±)-5-Chloro-6-(3-cyanophenyl)-4-cyclopentyl-1,4-dihydro-2H-3,1-benzoxazin-2-one(Compound 119), a pharmaceutically acceptable salt thereof, an ester thereof or an amide thereof.

22. The compound of claim 1, wherein the compound is (±)-5-Chloro-6-(3-cyanophenyl)-4-cyclopentyl-1,4-dihydro-2H-3,1-benzoxazin-2-thione (Compound 120), a pharmaceutically acceptable salt thereof, an ester thereof or an amide thereof.

23. The compound of claim 1, wherein the compound is (±)-5-Chloro-6-(3-cyanophenyl)-4-(3,4-difluorobenzyl)-1,4-dihydro-2H-3,1-benzoxazin-2-one (Compound 121), a pharmaceutically acceptable salt thereof, an ester thereof or an amide thereof.

24. The compound of claim 1, wherein the compound is(±)-5-Chloro-6-(3-cyanophenyl)-4-(3,4-difluorobenzyl)-1,4-dihydro-2H-3,1-benzoxazin-2-thione (Compound 122), a pharmaceutically acceptable salt thereof, an ester thereof or an amide thereof.

25. The compound of claim 1, wherein the compound is 5-Chloro-1,4-dihydro-6-(2,6-dimethoxyphenyl)-4,4-dimethyl-2H-3,1-benzoxazin-2-one (Compound 123), a pharmaceutically acceptable salt thereof, an ester thereof or an amide thereof.

26. The compound of claim 1, wherein the compound is 7-Chloro-6-(3-cyanophenyl)-1,4-dihydro-4,4-dimethyl-2H-3,1-benzoxazin-2-one (Compound 124), a pharmaceutically acceptable salt thereof, an ester thereof or an amide thereof.

27. The compound of claim 1, wherein the compound is 7-Chloro-6-(3-cyanophenyl)-1,4-dihydro-4,4-dimethyl-2H-3,1-benzoxazin-2-thione (Compound 125), a pharmaceutically acceptable salt thereof, an ester thereof or an amide thereof.

28. The compound of claim 1, wherein the compound is 7-Chloro-6-(3-cyano-2-methoxyphenyl)-1,4-dihydro-4,4-dimethyl-2H-3,1-benzoxazin-2-one (Compound 126), a pharmaceutically acceptable salt thereof, an ester thereof or an amide thereof.

29. The compound of claim 1, wherein the compound is 7-Chloro-6-(3-cyano-2-methoxyphenyl)-1,4-dihydro-4,4-dimethyl-2H-3,1-benzoxazin-2-thione (Compound 127), a pharmaceutically acceptable salt thereof, an ester thereof or an amide thereof.

30. The compound of claim 1, wherein the compound is 6-(3,5-Dimethylisoxazol-4-yl)-1,4-dihydro-4,4,8-trimethyl-2H-3,1-benzoxazin-2-one (Compound 128), a pharmaceutically acceptable salt thereof, an ester thereof or an amide thereof.

31. The compound of claim 1, wherein the compound is 1,4-Dihydro-6-(indol-7-yl)-4,4,8-trimethyl-2H-3,1-benzoxazin-2-one (Compound 129), a pharmaceutically acceptable salt thereof, an ester thereof or an amide thereof.

32. The pharmaceutical agent of claim 2, wherein the compounds is a compound of claim 3.

33. The pharmaceutical agent of claim 2, wherein the compounds is a compound of claim 4.

34. The pharmaceutical agent of claim 2, wherein the compounds is a compound of claim 5.

35. The pharmaceutical agent of claim 2, wherein the compounds is a compound of claim 6.

36. The pharmaceutical agent of claim 2, wherein the compounds is a compound of claim 7.

37. The pharmaceutical agent of claim 2, wherein the compounds is a compound of claim 8.

38. The pharmaceutical agent of claim 2, wherein the compounds is a compound of claim 9.

39. The pharmaceutical agent of claim 2, wherein the compounds is a compound of claim 10.

40. The pharmaceutical agent of claim 2, wherein the compounds is a compound of claim 11.

41. The pharmaceutical agent of claim 2, wherein the compounds is a compound of claim 12.

42. The pharmaceutical agent of claim 2, wherein the compounds is a compound of claim 13.

43. The pharmaceutical agent of claim 2, wherein the compounds is a compound of claim 14.

44. The pharmaceutical agent of claim 2, wherein the compounds is a compound of claim 15.

45. The pharmaceutical agent of claim 2, wherein the compounds is a compound of claim 16.

46. The pharmaceutical agent of claim 2, wherein the compounds is a compound of claim 17.

47. The pharmaceutical agent of claim 2, wherein the compounds is a compound of claim 18.

48. The pharmaceutical agent of claim 2, wherein the compounds is a compound of claim 19.

49. The pharmaceutical agent of claim 2, wherein the compounds is a compound of claim 20.

50. The pharmaceutical agent of claim 2, wherein the compounds is a compound of claim 21.

51. The pharmaceutical agent of claim 2, wherein the compounds is a compound of claim 22.

52. The pharmaceutical agent of claim 2, wherein the compounds is a compound of claim 23.

53. The pharmaceutical agent of claim 2, wherein the compounds is a compound of claim 24.

54. The pharmaceutical agent of claim 2, wherein the compounds is a compound of claim 25.

55. The pharmaceutical agent of claim 2, wherein the compounds is a compound of claim 26.

56. The pharmaceutical agent of claim 2, wherein the compounds is a compound of claim 27.

57. The pharmaceutical agent of claim 2, wherein the compounds is a compound of claim 28.

58. The pharmaceutical agent of claim 2, wherein the compounds is a compound of claim 29.

59. The pharmaceutical agent of claim 2, wherein the compounds is a compound of claim 30.

60. The pharmaceutical agent of claim 2, wherein the compounds is a compound of claim 31.

* * * * *